United States Patent
Mason et al.

(10) Patent No.: US 7,235,059 B2
(45) Date of Patent: Jun. 26, 2007

(54) RELEASABLY LOCKING HINGE FOR AN ORTHOPEDIC BRACE HAVING ADJUSTABLE ROTATION LIMITS

(75) Inventors: Jeffrey T. Mason, Escondido, CA (US); Paul Oddou, Oceanside, CA (US)

(73) Assignee: Breg, Inc., Vista, CA (US)

( * ) Notice: Subject to any disclaimer, the term of this patent is extended or adjusted under 35 U.S.C. 154(b) by 63 days.

(21) Appl. No.: 11/039,448

(22) Filed: Jan. 12, 2005

(65) Prior Publication Data

US 2006/0155230 A1  Jul. 13, 2006

(51) Int. Cl.
*A61F 5/00* (2006.01)
(52) U.S. Cl. ............... 602/26; 602/16; 602/23; 602/5; 128/882
(58) Field of Classification Search ........... 602/5, 602/26, 23, 16, 62; 128/882
See application file for complete search history.

(56) References Cited

U.S. PATENT DOCUMENTS

| | | | |
|---|---|---|---|
| 401,933 A | 4/1889 | De Camp | |
| 552,143 A | 12/1895 | Rankin | |
| 649,237 A | 5/1900 | Dyson | |
| 3,439,672 A | 4/1969 | Fisher | 128/88 |
| 3,805,773 A | 4/1974 | Sichau | 128/80 E |
| 4,481,941 A | 11/1984 | Rolfes | 128/87 R |
| 4,489,718 A | 12/1984 | Martin | 128/80 C |
| 4,531,515 A | 7/1985 | Rolfes | 128/87 R |
| 4,620,532 A | 11/1986 | Houswerth | 128/80 C |
| 4,655,201 A | 4/1987 | Pirmantgen | 128/80 C |
| 4,776,326 A | 10/1988 | Young et al. | 128/80 F |
| 4,817,588 A | 4/1989 | Bledsoe | 128/80 C |
| 4,982,732 A | 1/1991 | Morris | 128/80 C |
| 5,000,169 A | 3/1991 | Swicegood et al. | 128/80 C |
| 5,018,514 A | 5/1991 | Grood et al. | 128/80 C |
| 5,052,379 A | 10/1991 | Airy et al. | 128/80 C |
| 5,062,858 A | 11/1991 | Broeck et al. | 623/43 |
| 5,138,911 A | 8/1992 | Lan | 81/177.2 |
| 5,292,303 A | 3/1994 | Bastyr et al. | 602/16 |
| 5,409,449 A | 4/1995 | Nebolon | 602/16 |
| 5,443,444 A | 8/1995 | Pruyssers | 602/26 |
| 5,460,599 A | 10/1995 | Davis et al. | 602/26 |
| 5,653,680 A | 8/1997 | Cruz | 602/21 |
| 5,658,241 A | 8/1997 | Deharde et al. | 602/5 |
| 5,658,243 A | 8/1997 | Miller et al. | 602/26 |
| 5,672,152 A | 9/1997 | Mason et al. | 602/26 |
| 5,814,000 A | 9/1998 | Kilbey | 602/16 |
| 5,817,040 A | 10/1998 | Hess et al. | 602/26 |
| 5,827,208 A | 10/1998 | Mason et al. | 602/16 |
| 5,921,946 A | 7/1999 | Tillinghast et al. | 602/16 |
| 6,383,156 B1 | 5/2002 | Enzerink et al. | 602/16 |

(Continued)

*Primary Examiner*—Justine R. Yu
*Assistant Examiner*—Shumaya Ali
(74) *Attorney, Agent, or Firm*—Rodney F. Brown

(57) ABSTRACT

A hinge for an orthopedic brace has two rotation plates, a pivotal connector connecting the rotation plates, a rotation limiting mechanism, and a rotation locking mechanism. The rotation limiting mechanism includes a rotation limiting face formed in one of the rotation plates and a rotation limiting assembly which has a stop face engageable with the rotation limiting face upon rotation of the rotation plates in a given direction to limit further rotation in that direction. The rotation locking mechanism includes a series of lock notches formed in one of the rotation plates and a rotation lock pin positionable within one of the lock notches to lock the rotation plates in a fixed position.

19 Claims, 8 Drawing Sheets

U.S. PATENT DOCUMENTS

| | | | |
|---|---|---|---|
| 6,993,808 B1 * | 2/2006 | Bennett et al. | 16/334 |
| 7,037,287 B2 * | 5/2006 | Cormier et al. | 602/23 |
| 2002/0072695 A1 | 6/2002 | Doty et al. | 602/5 |
| 2002/0183672 A1 | 12/2002 | Enzerink et al. | 602/16 |

* cited by examiner

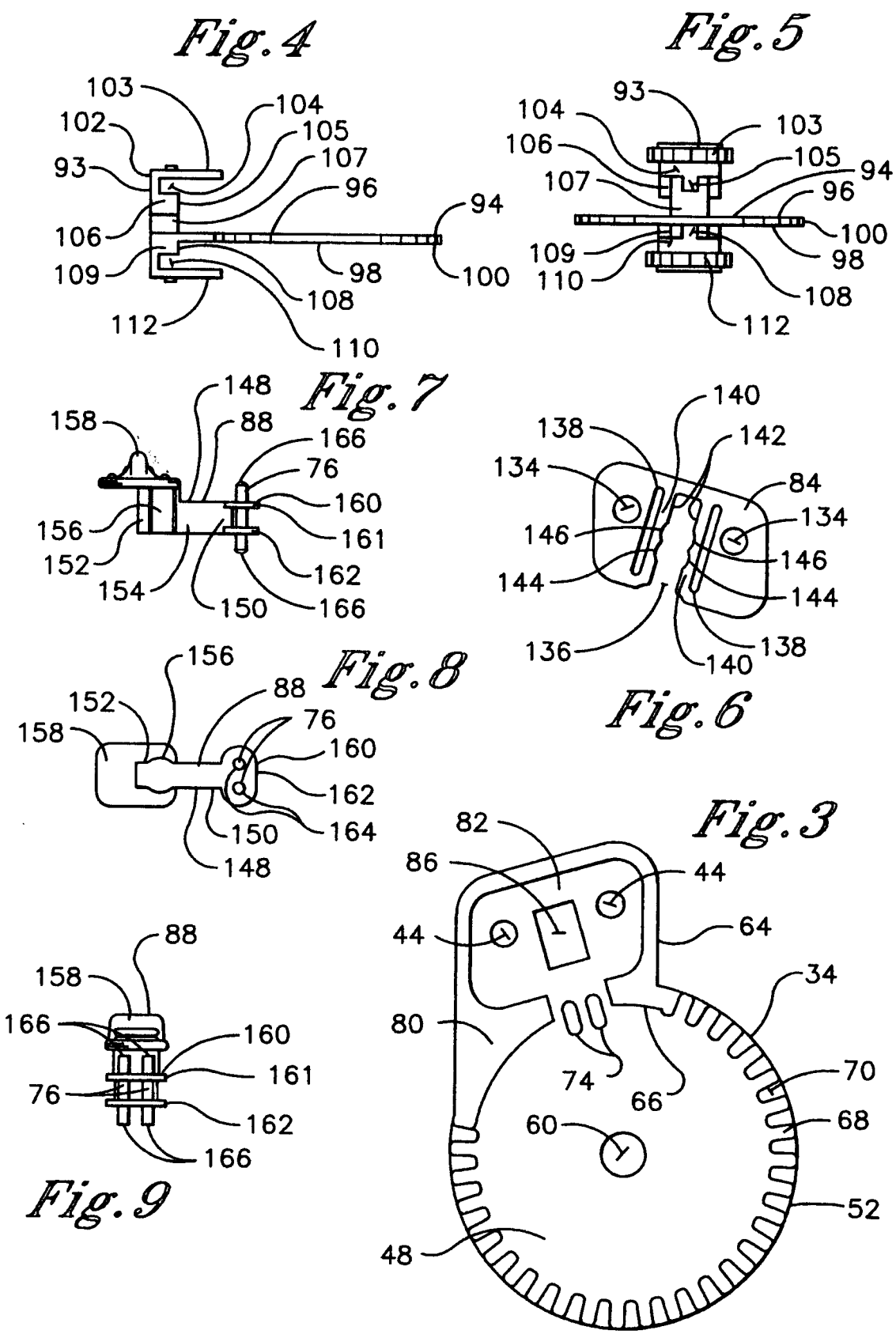

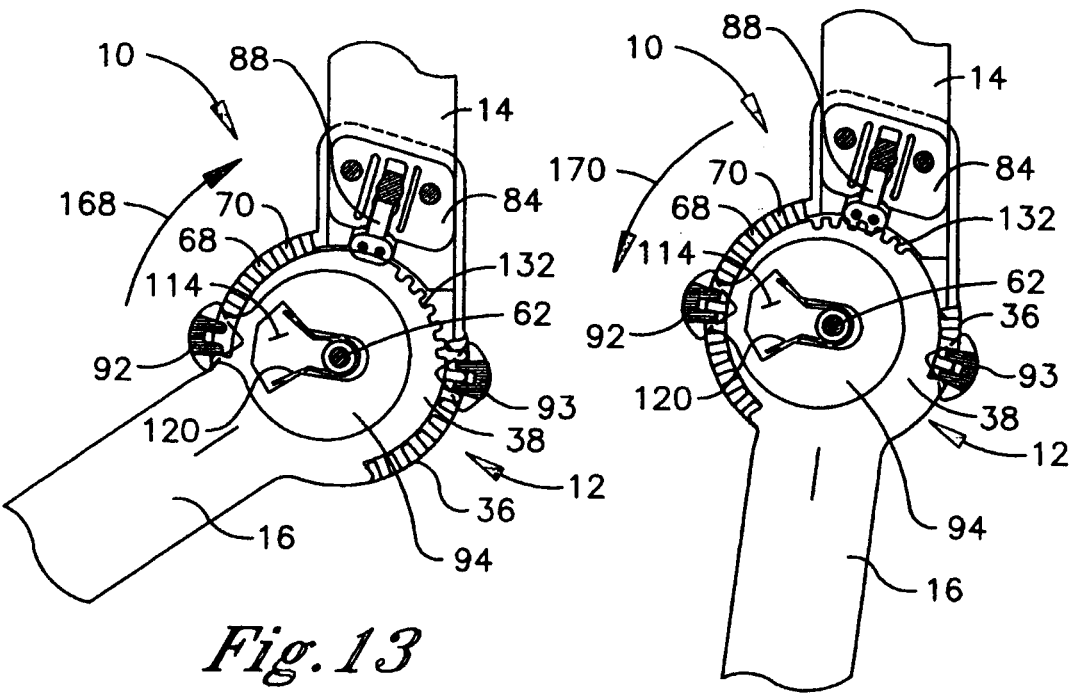
Fig. 13
Fig. 14
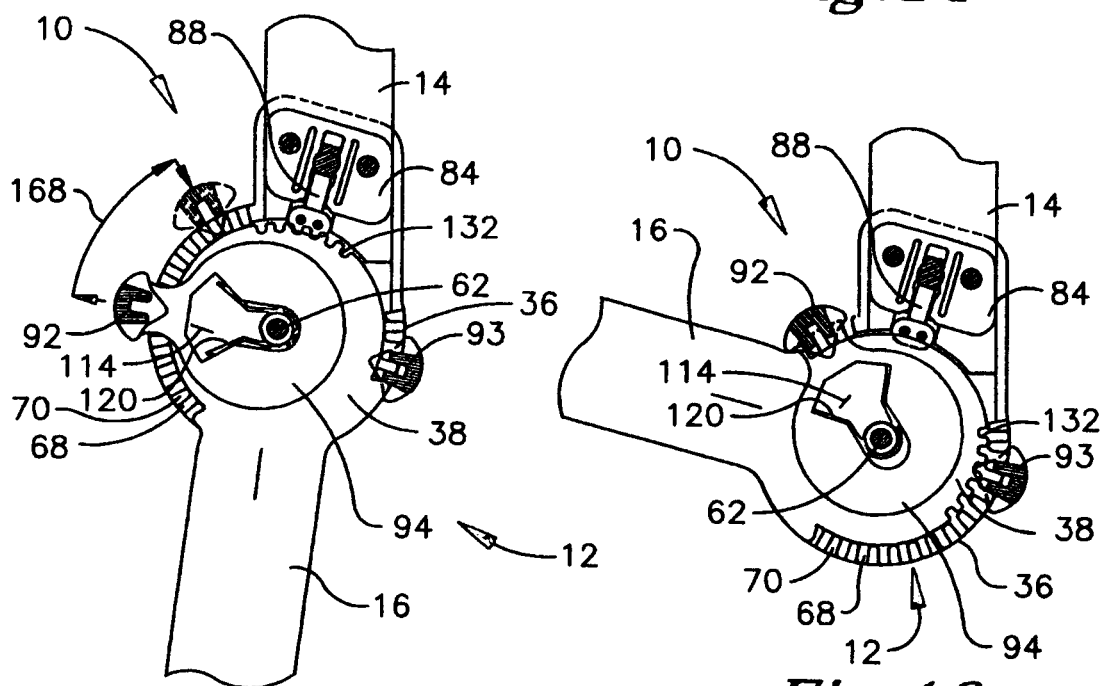
Fig. 15
Fig. 16

RELEASABLY LOCKING HINGE FOR AN ORTHOPEDIC BRACE HAVING ADJUSTABLE ROTATION LIMITS

TECHNICAL FIELD

The present invention relates generally to orthopedic braces, and more particularly to a hinge for an orthopedic brace, wherein the hinge has a mechanism for selectively adjusting the range of hinge rotation and a mechanism for releasably locking the hinge in a fixed position without altering the selected hinge rotation limits.

BACKGROUND OF THE INVENTION

Hinges for orthopedic braces having an adjustable rotation range in the extension and flexion direction are well known in the art. For example, U.S. Pat. No. 4,481,941 to Rolfes discloses a hinge having a pair of threaded screws, each being selectively threadably securable in one of a plurality of correspondingly threaded holes formed in the body of the hinge. The hinge rotation range is a function of screw placement insofar as securing a screw in a given hole determines a particular hinge rotation limit. The hinge rotation range is adjusted by changing the hinge rotation limit, which requires removal of the screw from its respective hole and placement of the screw in an alternate hole. However, It has been found that the task of adjusting the hinge rotation range can require a significant degree of dexterity to maneuver the relatively small screws into and out of the threaded holes. Furthermore, the screws are susceptible to being misplaced or lost during this task.

An alternate adjustable hinge disclosed by U.S. Pat. No. 401,933 to De Camp, substitutes pins for threaded screws as a means for setting the hinge rotation limit. The smooth surface of the pins enables them to slide in and out of the holes formed in the body of the hinge. The pins are secured in the holes by a leaf spring attached to each pin which biases the pin into its respective hole in a direction parallel to the axis of hinge rotation. Repositioning the pins of De Camp requires less dexterity than repositioning the screws of Rolfes. Nevertheless, De Camp still requires the user to pry the leaf spring away from the hinge body and remove the pin from the hole when adjusting the hinge rotation range. Accordingly, hinges having an improved adjustment mechanism were developed and disclosed in U.S. Pat. Nos. 5,672,152 and 5,827,208 to Mason et al.

The hinges of Mason et al. are relatively easy to set at a desired rotation limit in the extension or flexion direction and also have the desirable capability of being selectively lockable against rotation altogether. In accordance with one embodiment, the hinge of Mason et al. includes a plurality of rotation limiting notches and a locking notch formed in the peripheral edge of the hinge. A rotation limiting assembly is provided which is selectively positionable in one of the rotation limiting notches to define a hinge rotation limit. Alternatively, the rotation limiting assembly is selectively positionable in the locking notch to lock the hinge against rotation. The hinge also includes a biasing assembly which biases the rotation limiting assembly in a radially inward direction perpendicular to the axis of hinge rotation, thereby retaining the rotation limiting assembly in its selected rotation limiting position or locked position. The biasing assembly, however, enables elastic radial displacement of the rotation limiting assembly in a radially outward direction when a radially outward displacement force is externally applied thereto. The biasing assembly returns the rotation limiting assembly to a selected rotation limiting or locked position when the displacement force is withdrawn.

Although the above-recited hinge of Mason et al. is a substantial improvement over the hinges of De Camp and Rolfes, it is noted that the hinge of Mason et al. utilizes the same rotation limiting assembly for two different functions. In particular, the rotation limiting assembly is used to set a desired hinge rotation limit as well as to selectively lock the hinge against rotation altogether. Therefore, it is necessary to remove the rotation limiting assembly from its selected rotation limiting position and place the rotation limiting assembly in the locked position when it is desired to lock the hinge against rotation. When it is desired to enable rotation by unlocking the hinge, the rotation limiting assembly is removed from the locked position and returned to its selected rotation limiting position. This sequence of steps inherently increases the risk of erroneously resetting the hinge rotation limit when the rotation limiting assembly is returned to the rotation limiting position if the user has forgotten or improperly locates the prior prescribed hinge rotation limit. Therefore, a need exists for a hinge for an orthopedic brace having an adjustable rotation range, further wherein the hinge is selective between a locked mode and an unlocked mode of operation without disrupting the selected hinge rotation limits.

Accordingly, it is an generally an object of the present invention to provide a hinge for an orthopedic brace, which has an adjustable rotation range, and which has a locked and an unlocked mode of operation. More particularly, it is an object of the present invention to provide such a hinge having a rotation limiting mechanism, which selectively enables adjustment of the hinge rotation range, and also having a locking mechanism, which selectively enables locking the hinge against rotation altogether. It is still another object of the present invention to provide such a hinge, wherein the locking mechanism can be transitioned between the locked and unlocked modes without altering the rotation limits of the rotation limiting mechanism. These objects and others are accomplished in accordance with the invention described hereafter.

SUMMARY OF THE INVENTION

The present invention is a hinge for an orthopedic brace comprising a first rotation plate, a second rotation plate, a pivotal connector connecting the first and second rotation plates, a rotation limiting mechanism, and a rotation locking mechanism. The first rotation plate has a first peripheral edge, an inner face, and an outer face. The second rotation plate has a second peripheral edge.

The rotation limiting mechanism includes a rotation limiting face formed in the second peripheral edge and a rotation limiting assembly selectively positionable in a fixed position relative to the first rotation plate. The rotation limiting assembly has a stop face engageable with the rotation limiting face upon rotation of the second rotation plate relative to the first rotation plate in a first rotation direction, which substantially limits further rotation of the second rotation plate relative to the first rotation plate in the first rotation direction.

The rotation locking mechanism includes a rotation lock pin and a series of lock notches formed in the second peripheral edge. The rotation lock pin is selectively positionable within one of the series of lock notches, which substantially locks the first and second rotation plates against rotation of the second rotation plate relative to the first rotation plate in the first rotation direction or in a second rotation direction opposite the first rotation direction.

In accordance with specific embodiments, the rotation limiting mechanism includes a series of rotation limiting teeth formed in the inner face at the first peripheral edge. The rotation limiting assembly has an engagement face which is selectively positionable between two adjacent teeth of the series of teeth to place the rotation limiting assembly in the fixed position. The rotation limiting mechanism further includes a biasing member biasing the engagement face radially inward from the first peripheral edge.

The rotation locking mechanism includes a lock pin slot formed in the inner face and a lock actuator assembly engaging the rotation lock pin. The rotation lock pin is slidably positioned in the lock pin slot. The rotation lock pin has a longitudinal axis and the lock actuator assembly maintains the longitudinal axis of the rotation lock pin substantially perpendicular to the inner face. Alternatively or additionally, the lock pin slot has a longitudinal axis and the lock actuator assembly maintains the longitudinal axis of the rotation lock pin substantially perpendicular to the longitudinal axis of the lock pin slot.

The rotation lock pin is transitionable between a locked position and an unlocked position. The rotation lock pin is transitioned to the locked position by selectively positioning the rotation lock pin within one of the series of lock notches as recited above. The rotation lock pin is transitioned to the unlocked position by selectively withdrawing the rotation lock pin from one of the series of lock notches so that the rotation lock pin does not substantially impede rotation of the second rotation plate relative to the first rotation plate in the first or second rotation direction. The rotation lock pin can be transitionable between the locked and unlocked positions without substantially modifying the fixed position of the rotation limiting assembly.

The rotation locking mechanism further includes a lock transition plate and a lock actuator assembly engaging the rotation lock pin. The lock transition plate has a lock assembly cut-out and the lock actuator assembly has an actuator bar selectively and slidably positioned in the lock assembly cut-out. The lock assembly cut-out has a bordering edge with a first depression and a second depression formed therein and the actuator bar has a protrusion configured for close fitting within the first or second depression when the actuator bar is selectively slid within the lock assembly cut-out.

In accordance with an alternate embodiment, the present invention is a hinge for an orthopedic brace comprising a first external rotation plate, an internal rotation plate, a second external rotation plate, a pivotal connector connecting the first and second external rotation plates and internal rotation plate, a rotation limiting mechanism, and a rotation locking mechanism. The first external rotation plate has a first external peripheral edge, a first external inner face and a first external outer face. The internal rotation plate has an internal peripheral edge. The second external rotation plate has a second external peripheral edge, a second external inner face and a second external outer face.

The rotation limiting mechanism includes a series of rotation limiting teeth formed in the first external inner face at the first external peripheral edge, a rotation limiting face formed in the internal peripheral edge, and a rotation limiting assembly. The rotation limiting assembly has an engagement face selectively positionable between two adjacent teeth of the series of teeth to place the rotation limiting assembly in a fixed position. The rotation limiting assembly also has a stop face engageable with the rotation limiting face upon rotation of the internal rotation plate relative to the first external rotation plate in a first rotation direction which substantially limits further rotation of the internal rotation plate relative to the first external rotation plate in the first rotation direction.

The rotation locking mechanism includes a series of lock notches formed in the internal peripheral edge, a rotation lock pin, and a lock pin slot. The lock pin slot is formed in the first and second external inner faces, is formed only in the first external inner face, or is formed only in the second internal face. The rotation lock pin is slidably positioned in the lock pin slot and is selectively positionable within one of the series of lock notches, which substantially locks the first external rotation plate and the internal rotation plate against rotation of the internal rotation plate relative to the first external rotation plate in the first rotation direction or in a second rotation direction opposite the first rotation direction.

In accordance with a specific embodiment, the engagement face is a first engagement face and the rotation limiting mechanism further includes a series of rotation limiting teeth formed in the second external inner face at the second external peripheral edge. The rotation limiting assembly has a second engagement face selectively positionable between two adjacent teeth of the series of teeth in the second external inner face.

In accordance with another alternate embodiment, the present invention is a rotation locking mechanism for a hinge of an orthopedic brace. The hinge has a first rotation plate with a first peripheral edge, an inner face and an outer face, a second rotation plate with a second peripheral edge, and a pivotal connector connecting the first and second rotation plates. The rotation locking mechanism comprises a rotation lock pin, a series of lock notches formed in the second peripheral edge, and a lock pin slot formed in the inner face. The rotation lock pin is slidably positioned in the lock pin slot and is selectively positionable within one of the series of lock notches, which substantially locks the first and second rotation plates against rotation of the second rotation plate relative to the first rotation plate in a first rotation direction or in a second rotation direction opposite the first rotation direction.

The rotation locking mechanism further comprises a lock actuator assembly engaging the rotation lock pin. The rotation lock pin has a longitudinal axis and the lock actuator assembly maintains the longitudinal axis of the rotation lock pin substantially perpendicular to the inner face. The rotation locking mechanism further comprises a lock transition plate having a lock assembly cut-out. The lock actuator assembly has an actuator bar which is selectively and slidably positioned in the lock assembly cut-out. The lock assembly cut-out has a bordering edge with a first depression and a second depression formed therein and the actuator bar has a protrusion configured for close fitting within the first or second depression when the actuator bar is selectively slid within the lock assembly cut-out.

The rotation lock pin is transitionable between a locked position and an unlocked position. The rotation lock pin is transitioned to the locked position by selectively positioning the rotation lock pin within one of the series of lock notches as recited above. The rotation lock pin is transitioned to the unlocked position by selectively withdrawing the rotation lock pin from one of the series of lock notches so that the rotation lock pin does not substantially impede rotation of the second rotation plate relative to the first rotation plate in the first or second rotation direction.

The present invention will be further understood from the drawings and the following detailed description.

BRIEF DESCRIPTION OF THE DRAWINGS

FIG. 3 is a rear view of the inner face of a lateral exterior rotation plate included in the hinge of FIG. 1.

FIG. 4 is a side elevational view of a rotation limiting assembly included in the hinge of FIG. 1.

FIG. 5 is a front elevational view of a rotation limiting assembly included in the hinge of FIG. 1.

FIG. 6 is a top view of a lock transition plate included in the hinge of FIG. 1.

FIG. 7 is a side elevational view of a lock actuator assembly included in the hinge of FIG. 1.

FIG. 8 is a bottom view of a lock actuator assembly included in the hinge of FIG. 1.

FIG. 9 is a front elevational view of a lock actuator assembly included in the hinge of FIG. 1.

FIG. 13 is a cutaway frontal view of the hinge of FIG. 1, wherein the rotation limiting mechanism is in the rotation mode of operation and the rotation locking mechanism is in the unlocked mode of operation and further wherein the hinge is rotated in a clockwise direction to a preselected first flexion rotation limit.

FIG. 14 is a cutaway frontal view of the hinge of FIG. 1, wherein the rotation limiting mechanism is in the rotation mode of operation and the rotation locking mechanism is in the unlocked mode of operation and further wherein the hinge is rotated in a counterclockwise direction to a preselected first extension rotation limit.

FIG. 15 is a cutaway frontal view of the hinge of FIG. 1, wherein the rotation limiting mechanism is in the rotation limit adjustment mode of operation and the rotation locking mechanism is in the unlocked mode of operation and further wherein the flexion rotation limit of the hinge is being adjusted from the first flexion rotation limit of FIG. 13 to a second flexion rotation limit.

FIG. 16 is a cutaway frontal view of the hinge of FIG. 1, wherein the rotation limiting mechanism is in the rotation mode of operation and the rotation locking mechanism is in the unlocked mode of operation and further wherein the hinge is rotated in the clockwise direction to the second flexion rotation limit of FIG. 15.

DESCRIPTION OF PREFERRED EMBODIMENTS

Figure 1:
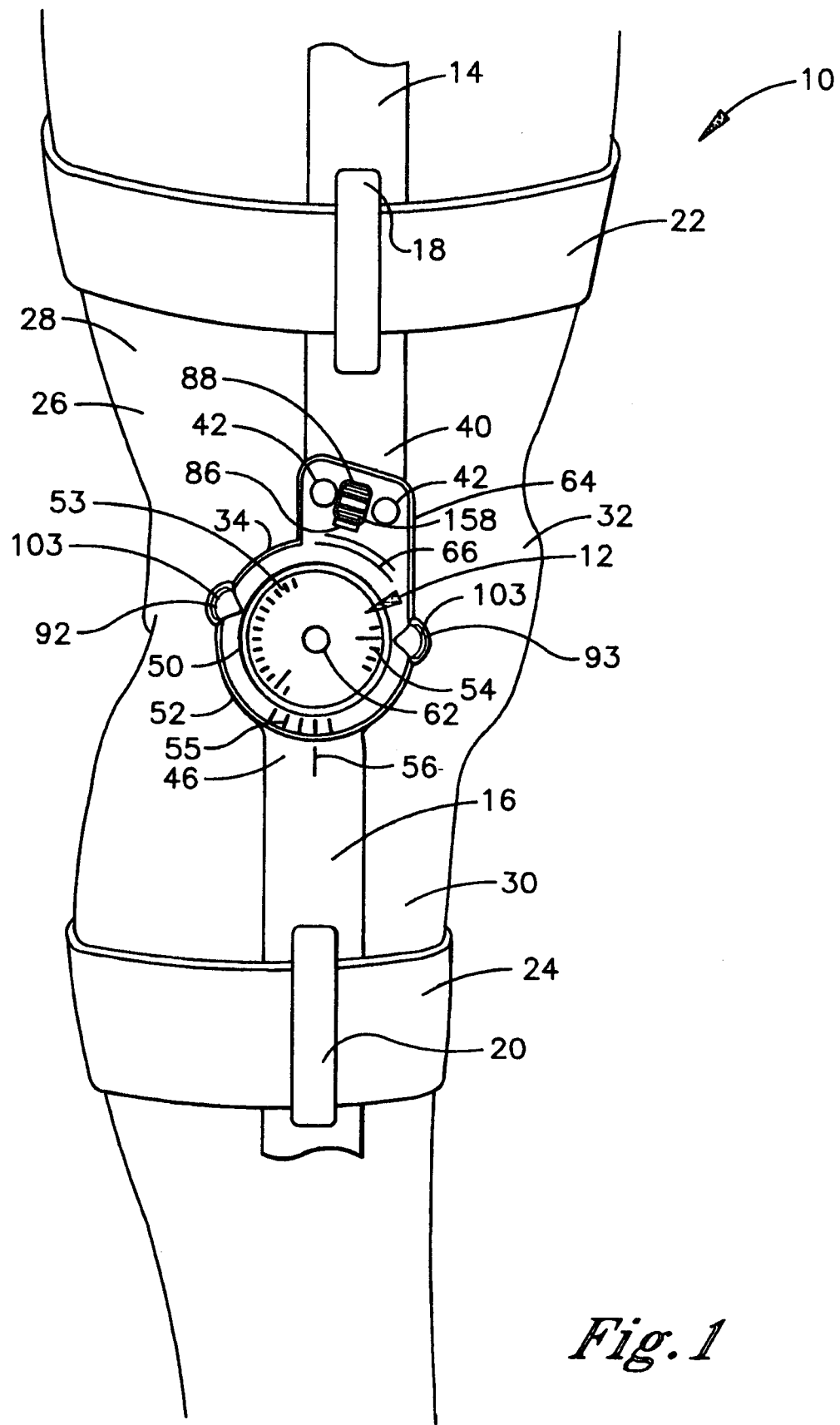
FIG. 1 is a side view of a leg having an orthopedic brace employing the hinge of the present invention mounted thereon.

Referring initially to FIG. 1, a hinged orthopedic brace is shown and generally designated 10. There are a number of relative terms defined below which are used in the following description to distinguish various elements of the brace 10 from one another, but which are not to be construed as limiting the scope of the invention.

The relative terms "medial" and "lateral" characterize certain elements of the brace 10, which are positioned about the axis of rotation of the brace 10. The terms describe the relative proximity of the given element to the central longitudinal axis of the body of the user when the brace 10 is mounted thereon. In particular, a "medial" element is closer to the central longitudinal axis of the body, while a "lateral" element is further from the central longitudinal axis of the body.

The relative terms "inner" and "outer" likewise characterize certain elements of the brace 10, which are positioned about the axis of rotation of the brace 10. However, the terms describe the relative proximity of the given element to the central longitudinal axis of the brace 10. An "inner" element is closer to the central longitudinal axis of the brace 10, while an "outer" element is further from the central longitudinal axis of the brace 10.

The terms "proximal" and "distal" characterize certain elements of the brace 10, which are aligned with the longitudinal axis of the brace 10. The terms describe the relative proximity of the given element to the axis of rotation of the brace 10. A "proximal" element is closer to the axis of rotation of the brace 10, while a "distal" element is further from the axis of rotation of the brace 10.

The terms "upper" and "lower" likewise characterize certain elements of the brace 10, which are aligned with the longitudinal axis of the brace 10. However, the terms describe the position of the given element as being either above or below a horizontal plane bisected by the axis of rotation of the brace 10. In particular, an "upper" element is above the horizontal plane bisecting the axis of rotation of the brace 10, while a "lower" element is below the horizontal plane bisecting the axis of rotation of the brace 10.

The hinged orthopedic brace 10 comprises a hinge 12, an upper rotation arm 14, a lower rotation arm 16, an upper strap retainer 18 associated with the upper rotation arm 14, and a lower strap retainer 20 associated with the lower rotation arm 16. The upper strap retainer 18 maintains an upper strap 22 distally connected to the upper rotation arm 14, while the lower strap retainer 20 maintains a lower strap 24 distally connected to the lower rotation arm 16.

For purposes of illustration, the hinged orthopedic brace 10 is a specific type of hinged orthopedic brace commonly termed a post-operative knee brace. The brace 10 is mounted on a right leg 26 of a user, which is characterized as having an upper leg 28, a lower leg 30 and a knee joint 32 rotationally connecting the upper and lower legs 28, 30. It is apparent to the skilled artisan that the post-operative knee brace 10 is alternatively adaptable for mounting on the left leg of a user. It is further apparent from the foregoing that the above-recited brace components 12, 14, 16, 18, 20, 22, 24 are readily adaptable to other types of hinged orthopedic braces for the knee and other joints of the body.

Both the upper and lower rotation arms 14, 16 are preferably relatively rigid, being formed from a lightweight, high-strength material, such as aluminum or stainless steel. When the brace 10 is mounted on the leg 26, the upper rotation arm 14 is longitudinally aligned with the lateral side of the upper leg 28, the hinge 12 is aligned with the lateral side of the knee joint 32 and the lower rotation arm 16 is longitudinally aligned with the lateral side of the lower leg 30. In particular, the longitudinal axis of the upper rotation arm 16 is oriented substantially parallel to the longitudinal axis of the upper leg 28 and is retained in removable engagement with the upper leg 28 by means of the upper strap 22 and upper strap retainer 18. The longitudinal axis of the lower rotation arm 16 is oriented substantially parallel to the longitudinal axis of the lower leg 30 and is retained in removable engagement with the lower leg 30 by means of the lower strap 24 and lower strap retainer 20.

Although not shown, it is within the scope of the present invention to provide relatively rigid, fitted, upper and lower leg cuffs attached to or integral with the upper and lower rotation arms 14, 16 which further secure the upper and lower rotation arms 14,16 to the upper and lower legs 28, 30, respectively. It is also within the scope of the present invention to provide additional straps and strap retainers which further secure the upper and lower rotation arms 14, 16 to the upper and lower legs 28, 30, respectively. It is further within the scope of the present invention to reverse the configuration of the brace 10 in a manner readily apparent to the skilled artisan so that the upper rotation arm 14 is repositioned in longitudinal alignment with the lateral side of the lower leg 30 and the lower rotation arm 16 is repositioned in longitudinal alignment with the lateral side of the upper leg 28, while the hinge 12 remains aligned with the lateral side of the knee joint 32. In another alternative, the upper rotation arm 14 can be longitudinally aligned with the medial side of the upper leg 28, the hinge 12 aligned with the medial side of the knee joint 32, and the lower rotation arm 16 longitudinally aligned with the medial side of the lower leg 30. This configuration can likewise be reversed so that the upper rotation arm 14 is repositioned in longitudinal alignment with the medial side of the lower leg 30 and the lower rotation arm 16 is repositioned in longitudinal alignment with the medial side of the upper leg 28, while the hinge 12 remains aligned with the medial side of the knee joint 32.

Figure 2A:
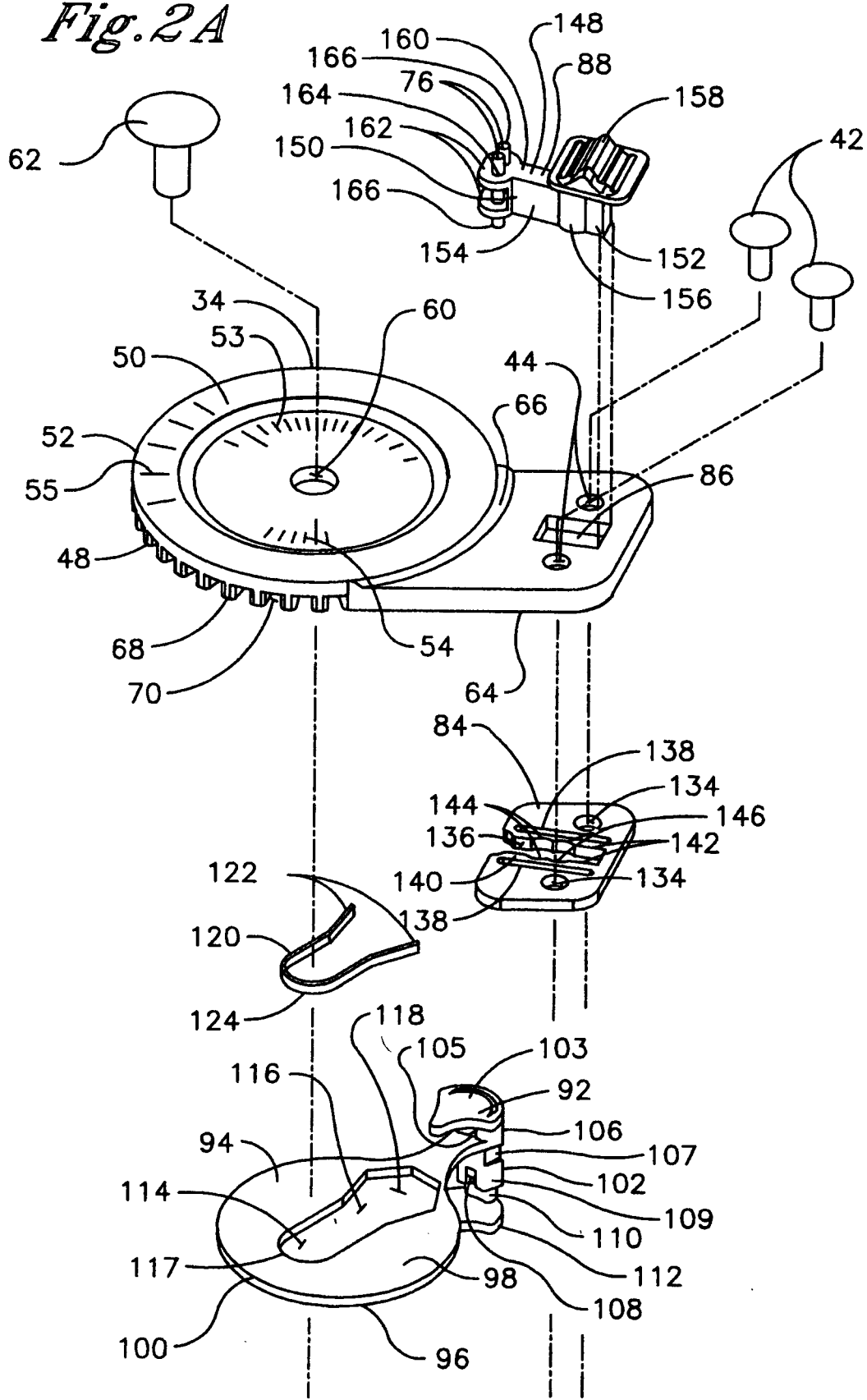
FIGS. 2A and 2B are an exploded perspective view of the hinge of FIG. 1.
Figure 2B:
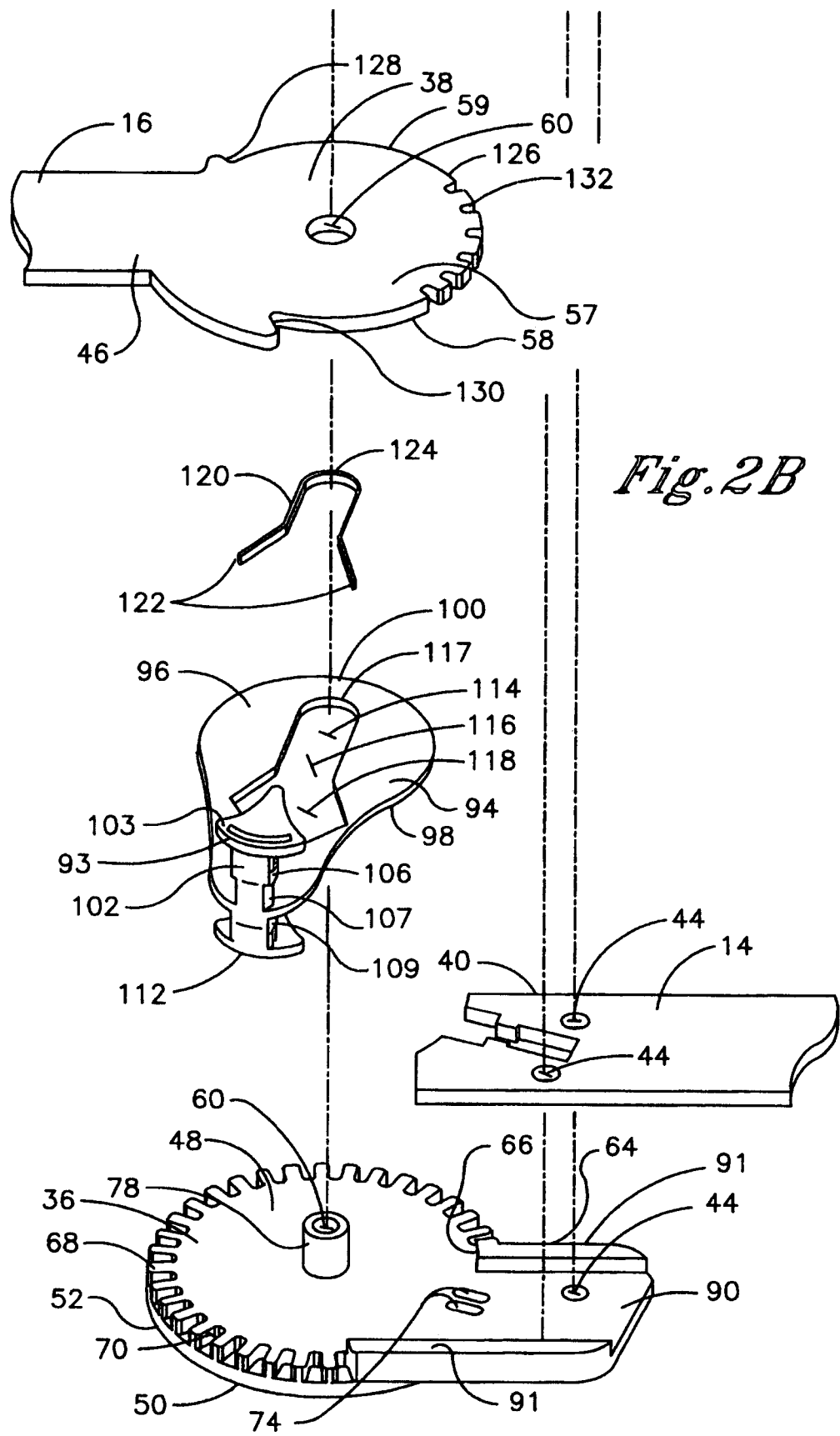

Referring additionally to FIGS. 2A and 2B, the hinge 12 comprises a lateral exterior rotation plate 34, a medial exterior rotation plate 36, and an interior rotation plate 38 rotatably positioned between the lateral and medial exterior rotation plates 34, 36. The lateral and medial exterior rotation plates 34, 36 are fixably fastened to a proximal end 40 of the upper rotation arm 14 by conventional fasteners 42, such as rivets or the like, which extend through fastening apertures 44 provided in the exterior rotation plates 34, 36. The interior rotation plate 38 is integral with the lower rotation arm 16, being contiguous with a proximal end 46 of the lower rotation arm 16.

Although not shown, alternate constructions of the rotation plates 34, 36, 38 in association with the rotation arms 14,16 are within the scope of the present invention. For example, one or both of the lateral and medial exterior rotation plates 34, 36 may be integral with the upper rotation arm 14, while the interior rotation plate 38 is fixably fastened to the lower rotation arm 16. Alternatively, one or both of the lateral and medial exterior rotation plates 34, 36 may be integral with the upper rotation arm 14, while the interior rotation plate 38 is similarly integral with the lower rotation arm 16. In yet another alternative, the interior rotation plate 38 may be fixably fastened to the lower rotation arm 16, while the lateral and medial exterior rotation plates 34, 36 are similarly fixably fastened to the upper rotation arm 14.

The lateral and medial exterior rotation plates 34, 36 are both preferably formed from a relatively rigid, lightweight, high-strength material, such as a plastic, while the interior rotation plate 38 is preferably formed from the same material as the lower rotation arm 16. Referring additionally to FIG. 3, each exterior rotation plate 34, 36 has a substantially similar circular configuration with an inner face 48 and an outer face 50, which are bounded by a peripheral edge 52. A plurality of flexion rotation limit markers 53, extension rotation limit markers 54, and rotation lock markers 55 are preferably provided on the outer face 50 of the lateral exterior rotation plate 34. A lock reference marker 56 is preferably provided on the proximal end 46 of the lower rotation arm 16.

Each flexion rotation limit marker 53 displays a specific flexion rotation limit value (e.g., 0°, 30°, etc.), which correlates to the flexion angle of the upper and lower rotation arms 14,16, and correspondingly of the knee joint 32, when the hinge 12 reaches the specific flexion rotation limit corresponding to that value in a manner described hereafter. Each extension rotation limit marker 54 similarly displays a specific extension rotation limit value (e.g., 0°, 30°, etc.), which correlates to the extension angle of the upper and lower rotation arms 14, 16, and correspondingly of the knee joint 32, when the hinge 12 reaches the specific extension rotation limit corresponding to that value in a manner described hereafter. Each rotation lock marker 55 displays a specific lock position value (e.g., 0°, 30°, etc., and further characterized as either flexion or extension), which correlates to the flexion or extension angle of the upper and lower rotation arms 14, 16, and correspondingly of the knee joint 32, when the hinge 12 is locked in the specific lock position corresponding to that value (expressed as a flexion or extension angle) in a manner described hereafter.

The peripheral edge 52 defines the circumference of each exterior rotation plate 34, 36. The inner face 48 of each exterior rotation plate 34, 36 is preferably a smooth, flat, low-friction surface. The interior rotation plate 38 likewise has a substantially circular configuration with a lateral face 57 and a medial face 58, which are bounded by a peripheral edge 59. The peripheral edge 59 defines the circumference of the interior rotation plate 38. The lateral and medial faces 57, 58 of the interior rotation plate 38 are preferably smooth, flat, low-friction surfaces.

Each of the rotation plates 34, 36, 38 is provided with a centrally-positioned pivot aperture 60 extending therethrough. A pivot member 62, having a diameter smaller than the pivot apertures 60, extends through all of the pivot apertures 60 and is fixably, but rotatably, retained therein. As such, the exterior rotation plates 34, 36 are freely rotatable in unison about the pivot member 62 relative to the interior rotation plate 36 when not impeded by the rotation limiting and locking mechanisms of the hinge 12 described hereafter. A preferred pivot member 62 is a rivet having a narrow body and flattened heads at either end, which engage the outer faces 50 of the lateral and medial exterior rotation plates 34, 36, respectively. A bushing (not shown) may also be provided which encloses the body of the pivot member 62 and eases rotation of the rotation plates 34, 36, 38 about the pivot member 62.

Each exterior rotation plate 34, 36 has an integrally-formed fastening extension 64 extending from a segment 66 of the peripheral edge 52. The fastening extension 64 includes the fastening apertures 44 and provides a base for fastening the exterior rotation plates 34, 36 to the proximal end 40 of the upper rotation arm 14 as described above. A plurality of rotation limiting teeth 68 are circumferentially formed at uniform periodically spaced intervals in the inner face 48 of each exterior rotation plate 34, 36 at the peripheral edges 52. The rotation limiting teeth 68 extend in a continuum along the peripheral edge 52 except where the fastening extension 64 extends from the peripheral edge 52.

Each rotation limiting tooth 68 of the lateral exterior rotation plate 34 is aligned at all times with a uniquely corresponding rotation limiting tooth 68 of the medial exterior rotation plate 36 when the hinge 12 is assembled. Furthermore, each rotation limiting tooth 68 of the lateral exterior rotation plate 34 and corresponding rotation limiting tooth 68 of the medial exterior rotation plate 36 is uniquely correlated with a specific flexion or extension rotation limit of the hinge 12. As such, each flexion rotation limit marker 53 displaying a given flexion rotation limit value is uniquely aligned with the rotation limiting tooth 68 correlated with that given flexion rotation limit. Similarly, each extension rotation limit marker 54 displaying a given extension rotation limit value is uniquely aligned with the rotation limiting tooth 68 correlated with that given extension rotation limit.

The rotation limiting teeth 68 each have an identical configuration and are radially aligned relative to the exterior rotation plate 34, 36. Each adjacent pair of rotation limiting teeth 68 on the lateral exterior rotation plate 34 defines a receiving space 70 therebetween and each adjacent pair of rotation limiting teeth 68 on the medial exterior rotation plate 36 likewise defines a receiving space 70 therebetween. Each receiving space 70 of the lateral exterior rotation plate 34 is aligned at all times with a uniquely corresponding receiving space 70 of the medial exterior rotation plate 36 when the hinge 12 is assembled. The rotation limiting teeth 68 and receiving spaces 70 shown herein each has an essentially U-shaped profile, but it is understood that other configurations of the rotation limiting teeth and receiving spaces are possible within the scope of the present invention.

A pair of closely-spaced, side-by-side lock pin slots 74 are also formed in the inner face 48 of each exterior rotation plate 34, 36. Each lock pin slot 74 has an identical closed-ended configuration with an oval shape and each is configured to receive a rotation lock pin 76 in a manner described hereafter. The lock pin slots 74 are positioned at the peripheral edge 52 of each exterior rotation plate 34, 36 along the segment 66 of the peripheral edge 52 from which the fastening extension 64 extends. The lock pin slots 74, like the rotation limiting teeth 68, extend radially relative to the exterior rotation plates 34, 36. Furthermore, each lock pin slot 74 of the lateral exterior rotation plate 34 is aligned at all times with the uniquely corresponding lock pin slot 74 of the medial exterior rotation plate 36 when the hinge 12 is assembled.

Although the exterior rotation plates 34, 36 have a substantially similar construction, as described above, there are some structural distinctions between the lateral and medial exterior rotation plates 34, 36 which facilitate the function of the hinge 12. In particular, the medial exterior rotation plate 36 has an integrally-formed pivot housing 78 positioned on the inner face 48 at the pivot aperture 60. In contrast, the lateral exterior rotation plate 34 is devoid of any additional structure at the pivot aperture 60 so that the inner face 48 of the lateral exterior rotation plate 34 transitions directly into the pivot aperture 60.

The pivot housing 78 is a tubular member which extends away from the inner face 48 about the rotation axis of the medial exterior rotation plate 36. The pivot housing 78 has an open passageway, which is continuous with the pivot aperture 60 of the medial exterior rotation plate 36. The open passageway of the pivot housing 78 also aligns with the pivot aperture 60 of the lateral exterior rotation plate 34. The pivot aperture 60 of the lateral exterior rotation plate 34 is slightly larger than the pivot aperture 60 of the medial exterior rotation plate 36 so that the outer wall of the pivot housing 78 is close-fittingly received into the pivot aperture 60 of the lateral exterior rotation plate 34 when the hinge 12 is assembled.

The configuration of the fastening extensions 64 also differs between the lateral and medial exterior rotation plates 34, 36, respectively. The fastening extension 64 of the lateral exterior rotation plate 34 has an inner face 80 which is raised relative to the remainder of the inner face 48 of the lateral exterior rotation plate 34. The raised inner face 80 includes a transition plate indentation 82 for receiving a lock transition plate 84 therein in a manner described hereafter. An actuator aperture 86 is also provided through the fastening extension 64 of the lateral exterior rotation plate 34, which is positioned between the fastening apertures 44, for receiving a lock actuator assembly 88 therein in a manner described hereafter. In contrast, the fastening extension 64 of the medial exterior rotation plate 36 has an inner face 90 which is relatively level with the remainder of the inner face 48 with the exception of raised rails 91 which extend along the edges of the fastening extension 64 away from the center of the medial exterior rotation plate 36.

The rotation limiting mechanism of the hinge 12 includes the rotation limiting teeth 68 and receiving spaces 70 of the exterior rotation plates 34, 36, a flexion rotation limiting assembly 92, an extension rotation limiting assembly 93, and elements of the peripheral edge 59 of the interior rotation plate 38 described hereafter. Referring additionally to FIGS. 4 and 5, the extension rotation limiting assembly 93 comprises a rotation limiting assembly plate 94 having a substantially circular planar configuration with an inner face 96 and an outer face 98 which are bounded by a peripheral edge 100. The peripheral edge 100 defines the circumference of the rotation limiting assembly plate 94, which is preferably smaller than the circumference of the exterior rotation plates 34, 36. The inner and outer faces 96, 98 of the rotation limiting assembly plate 94 are preferably smooth, flat, low-friction surfaces.

The extension rotation limiting assembly 93 further comprises a stop post 102 affixed to the peripheral edge 100 of the rotation limiting assembly plate 94. The longitudinal axis of the stop post 102 is aligned essentially perpendicular to the planar faces 96, 98 of the rotation limiting assembly plate 94. The stop post 102 is serially segmented into a lateral head 103, a lateral stop slot 104, a lateral tooth slot 105 and bounding lateral engagement faces 106, a stop face 107, a medial tooth slot 108 and bounding medial engagement faces 109, a medial stop slot 110, and a medial head 112.

A central portion of the stop post 102 is affixed to the peripheral edge 100 of the rotation limiting assembly plate 94, preferably at the intersection of the stop face 107 and the lateral engagement faces 106 or at the intersection of the stop face 107 and the medial engagement faces 109. As such, the lateral head 103, lateral stop slot 104, lateral tooth slot 105, lateral engagement faces 106, and stop face 107 are on one side of the rotation limiting assembly plate 94, while the medial tooth slot 108, medial engagement faces 109, medial stop slot 110, and medial head 112 are on the opposite side of the rotation limiting assembly plate 94, or alternatively the lateral head 103, lateral stop slot 104, lateral tooth slot 105, and lateral engagement faces 106 are on one side of the rotation limiting assembly plate 94, while the stop face 107, medial tooth slot 108, medial engagement faces 109, medial stop slot 110, and medial head 112 are on the opposite side of the rotation limiting assembly plate 94.

The stop face 107 is defined by a notch formed in the stop post 102 between the lateral and medial engagement faces 106, 109. As such, the stop face 107 has a concave configuration relative to the lateral and medial engagement faces 106, 109. The height of the stop face 107 is preferably slightly greater than the height of the interior rotation plate 38 (i.e., the thickness of the peripheral edge 59) to receive the peripheral edge 59 therein.

The lateral stop slot 104 and peripheral edge 52 of the lateral exterior rotation plate 34 are cooperatively configured so that the lateral stop slot 104 receives a portion of the peripheral edge 52 which is aligned with a receiving space 70. In particular, the lateral stop slot 104 and peripheral edge 52 are configured such that the height of the lateral stop slot 104 is slightly greater than the thickness of the portions of the peripheral edge 52 aligned with the receiving spaces 70. The rotation limiting teeth 68 and lateral tooth slot 105 are cooperatively configured so that a desired rotation limiting tooth 68 fits within the lateral tooth slot 105. The receiving spaces 70 and lateral engagement faces 106 are likewise cooperatively configured so that each lateral engagement face 106 fits within a desired receiving space 70 adjacent to the rotation limiting tooth 68 in the lateral tooth slot 105. The lateral head 103 is manually accessible to a user at a position adjacent to the outer face 50 of the lateral exterior rotation plate 34.

The medial stop slot 110 and peripheral edge 52 of the medial exterior rotation plate 36 are similarly cooperatively configured so that the medial stop slot 110 receives a portion of the peripheral edge 52 which is aligned with a receiving space 70. The rotation limiting teeth 68 and medial tooth slot 108 are cooperatively configured so that a desired rotation limiting tooth 68 fits within the medial tooth slot 108. The receiving spaces 70 and medial engagement faces 109 are likewise cooperatively configured so that each medial engagement face 109 fits within a desired receiving space 70 adjacent to the rotation limiting tooth 68 in the medial tooth slot 108. The medial head 112 is manually accessible to a user at a position adjacent to the outer face 50 of the medial exterior rotation plate 36.

A spring cut-out 114 is formed through the rotation limiting assembly plate 94. The spring cut-out 114 has a relatively narrow central channel 116, which has a closed end 117 and an opposite open end continuous with an adjoining relatively wide peripheral channel 118. The pivot member 62 and pivot housing 78 are received within the central channel 116, the width of the central channel 116 being only slightly greater than the outside diameter of the pivot housing 78. As such, the rotation limiting assembly plate 94 is freely rotatable about the pivot member 62 and pivot housing 78 relative to the rotation plates 34, 36, 38 when not impeded by the rotation limiting and locking mechanisms of the hinge 12. In contrast, the length of the central channel 116 is substantially greater than the outside diameter of the pivot housing 78. As such, the rotation limiting assembly plate 94 is also displaceable in a linear path about the pivot member 62 and pivot housing 78 along the length of the central channel 116 between a fixed position, which enables a rotation mode of operation of the rotation limiting mechanism of the hinge 12, and a rotation limit adjustment position, which enables a rotation limit adjustment mode of operation of the rotation limiting mechanism of the hinge 12, as described hereafter. However, the rotation limiting assembly plate 94 is essentially not linearly displaceable about the pivot member 62 and pivot housing 78 along the width of the central channel 116.

A leaf spring 120 is provided, which is configured to conform to the profile of the spring cut-out 114 and is positioned therein. The leaf spring 120 has two straight end segments 122 joined by a U-shaped middle segment 124. The end segments 122 of the leaf spring 120 engage the walls of the peripheral channel 118, while the middle segment 124 of the leaf spring 120 engages the walls of the central channel 116 and the pivot housing 78. The leaf spring 120 biases the rotation limiting assembly plate 94 in the fixed position. When the rotation limiting assembly plate 94 is in the fixed position, the lateral and medial engagement faces 106, 109 of the stop post 102 are received within correspondingly aligned receiving spaces 70 of the lateral and medial external rotation plates 34, 36 and the rotation limiting teeth 68 are received within correspondingly aligned lateral and medial tooth slots 105, 108. The lateral and medial engagement faces 106, 109 and rotation limiting teeth 68 are retained in their respective positions by the radially-inward directed biasing force of the leaf spring 120. Engagement of the lateral and medial engagement faces 106, 109 and the rotation limiting teeth 68 prevents rotational displacement of the extension rotation limiting assembly 93 about the pivot member 62 relative to the rotation plates 34, 36, 38.

The rotation limiting assembly plate 94 can be transitioned to the rotation limit adjustment position by applying a spring tensioning displacement force to the rotation limiting assembly plate 94 in a radially outward direction aligned with the longitudinal axis of the central channel 116. The displacement force is preferably applied to the rotation limiting assembly plate 94 by manually gripping the lateral and medial heads 103, 112 of the extension rotation limiting assembly 93 and pulling the lateral and medial heads 103, 112 radially outward. When the radially outward displacement force exceeds the biasing force of the leaf spring 120, the displacement force displaces the rotation limiting assembly plate 94 radially outward to withdraw the lateral and medial engagement faces 106, 109 from the receiving spaces 70 and the rotation limiting teeth 68 from the lateral and medial tooth slots 105, 108. As long as a sufficient displacement force is maintained on the rotation limiting assembly plate 94, the rotation limiting assembly plate 94 is retained in the rotation limit adjustment position and the extension rotation limiting assembly 93 is freely rotatable about the pivot member 62 relative to the rotation plates 34, 36, 38. Once the displacement force is withdrawn, the biasing force of the leaf spring 120 returns the rotation limiting assembly plate 94 to the fixed position, which prevents further rotational displacement of the extension rotation limiting assembly 93 about the pivot member 62 relative to the rotation plates 34, 36, 38.

The rotation limiting assembly plate 94 and stop post 102 are preferably integrally formed as a single unitary structure from a relatively rigid, lightweight, high-strength material, such as a plastic, which is the same or similar to that used to form the exterior rotation plates 34, 36. The leaf spring 120 is preferably a separate relatively elastic band formed from a lightweight, high-strength material, such as a malleable metal, e.g., copper.

The flexion rotation limiting assembly 92 is substantially identical to the extension rotation limiting assembly 93 except that the orientation of the flexion rotation limiting assembly 92 is flipped 180° relative to the extension rotation limiting assembly 93 so that both rotation limiting assemblies 92, 93 can be rotated about the pivot member 62 and pivot housing 78 relative to the rotation plates 34, 36, 38 without interfering with one another. Accordingly, the flexion rotation limiting assembly 92 has a rotation limiting assembly plate, stop post and leaf spring which are essentially identical in structure and function to those of the extension rotation limiting assembly 93 described above and, as such, are identified by the same reference characters.

When the hinge 12 is assembled, the inner face 48 of the lateral exterior rotation plate 34 adjoins the outer face 98 of the rotation limiting assembly plate 94 of the flexion rotation limiting assembly 92. The innerface 96 of the rotation limiting assembly plate 94 of the flexion rotation limiting assembly 92 adjoins the lateral face 57 of the interior rotation plate 38. The inner face 48 of the medial exterior rotation plate 36 adjoins the outer face 98 of the rotation limiting assembly plate 94 of the extension rotation limiting assembly 93. The inner face 96 of the rotation limiting assembly plate 94 of the extension rotation limiting assembly 93 adjoins the medial face 58 of the interior rotation plate 38.

Although not shown, the hinge 12 can alternately be assembled so that the inner face 48 of the lateral exterior rotation plate 34 adjoins the outer face 98 of the rotation limiting assembly plate 94 of the extension rotation limiting assembly 93. The inner face 96 of the rotation limiting assembly plate 94 of the extension rotation limiting assembly 93 adjoins the lateral face 57 of the interior rotation plate 38. The inner face 48 of the medial exterior rotation plate 36 adjoins the outer face 98 of the rotation limiting assembly plate 94 of the flexion rotation limiting assembly 92. The inner face 96 of the rotation limiting assembly plate 94 of the flexion rotation limiting assembly 92 adjoins the medial face 58 of the interior rotation plate 38.

The peripheral edge 59 of the interior rotation plate 38 has a rotation arc 126 of about 270°. The rotation arc 126 is bounded on one end by a flexion rotation limiting face 128, which functions in cooperation with the engagement faces 106, 109 of the flexion rotation limiting assembly 92 in a manner described hereafter. The rotation arc 126 is bounded on the opposite end by an extension rotation limiting face 130, which correspondingly functions in cooperation with the engagement faces 106, 109 of the extension rotation limiting assembly 93. The rotation arc 126 additionally has a plurality of lock notches 132 circumferentially formed in the peripheral edge 59 at spaced intervals along the rotation arc intermediately between the flexion and extension rotation limiting faces 128, 130. The lock notches 132 of the interior rotation plate 38 are elements of the rotation locking mechanism, which function in cooperation with the remaining elements of the rotation locking mechanism described hereafter.

In addition to the lock notches 132, the rotation locking mechanism of the hinge 12 includes the lock pin slots 74 of the exterior rotation plates 34, 36, the rotation lock pins 76, the lock transition plate 84, and the lock actuator assembly 88. Referring additionally to FIG. 6, the lock transition plate 84 is a planar structure which is sized and configured to nest within the transition plate indentation 82 flush with the inner face 90 of the fastening extension 64 of the medial exterior rotation plate 36. A pair of fastening apertures 134 are formed through the lock transition plate 84, which correspond to the fastening apertures 44 of the exterior rotation plates 34, 36. The fastening apertures 134 are in alignment with the fastening apertures 44 when the hinge 12 is assembled, to receive the fasteners 42 therein. A lock assembly cut-out 136 and a pair of expansion slots 138 are also formed through the lock transition plate 84.

The lock assembly cut-out 136 has an open end, a closed end and two parallel sides. The expansion slots 138 are closely positioned adjacent to the opposite sides of the lock assembly cut-out 136 and are essentially parallely aligned with one another and with the lock assembly cut-out 136. The small separation distance between each expansion slot 138 and the lock assembly cut-out 136 defines an expansion rail 140, which is a narrow strip of relatively flexible material. The edge 142 of each expansion rail 140 bordering the lock assembly cut-out 136 defines the parallel sides of the lock assembly cut-out 136. Each bordering edge 142 has a relatively smooth linear surface with the exception of an arcuately-shaped proximal indentation 144 and an arcuately-shaped distal indentation 146 formed adjacent to one another in the bordering edge 142. The proximal and distal indentations 144, 146 of the opposing bordering edges 142 are positioned in direct corresponding alignment with one another across the lock assembly cut-out 136. The lock transition plate 84 is preferably integrally formed as a single unitary structure from a relatively elastic, lightweight, high-strength material, such as a plastic.

Referring additionally to FIGS. 7–9, the lock actuator assembly 88 comprises an actuator bar 148 having a proximal end 150, a distal end 152, and longitudinal sides 154 connecting the two ends 150, 152. The longitudinal sides 154 have a relatively smooth linear surface with the exception of an arcuate protrusion 156 formed on each longitudinal side 154 of the actuator bar 148 near the distal end 152. Each protrusion 156 is sized and configured in correspondence with the proximal and distal indentations 144, 146 of the lock transition plate 84, so that the contour of the protrusion 156 conforms closely to the contour of either the proximal indentation 144 or the distal indentation 146 when the protrusion 156 is positioned in one of the indentations 144 or 146. The actuator bar 148 is slidably retained in the lock assembly cut-out 136, wherein the longitudinal sides 154 of the actuator bar 148 are essentially parallely aligned with the bordering edges 142 of the expansion rails when the hinge 12 is assembled.

A manually accessible actuator grip 158 is positioned adjacent to the outer face 50 of the lateral exterior rotation plate 34 and is connected to the distal end 152 of the actuator bar 148 through the actuator aperture 86 of the lateral exterior rotation plate 34. A lock pin retainer 160 is mounted on the proximal end 150 of the actuator bar 148. The lock pin retainer 160 includes a lateral pin retainer plate 161 and a medial pin retainer plate 162 positioned one atop the other and spaced a distance apart, which corresponds approximately to the thickness of the interior rotation plate 38. Each pin retainer plate 161, 162 has a pair of side-by-side pin apertures 164 formed therethrough and spaced a distance apart, which corresponds to the distance between the closely-spaced lock pin slots 74. Accordingly, there are a total of four pin apertures 164, two in the lateral pin retainer plate 161 and two in the medial pin retainer plate 162.

One of the two rotation lock pins 76 is fixably mounted within the two pin apertures 164 aligned one atop the other in the two pin retainer plates 161, 162 and the remaining rotation lock pin 76 is fixably mounted within the remaining two vertically-aligned pin apertures 164. The ends 166 of each rotation lock pin 76 extend beyond the pin retainer plates 161, 162. One extended end 166 of each rotation lock pin 76 is slidably positioned in the adjoining lock pin slots 74 of the lateral exterior rotation plate 34 when the hinge 12 is assembled and the opposite extended end 166 of each rotation lock pin 76 is slidably positioned in the adjoining lock pin slots 74 of the medial exterior rotation plate 36. Each lock pin slot 74 and rotation lock pin 76 has a longitudinal axis. The longitudinal axes of the rotation lock pins 76 are aligned perpendicular to the inner faces of the 48 of the lateral and medial exterior rotation plates 34, 36 and are likewise aligned perpendicular to the longitudinal axes of the lock pin slots 74.

The actuator bar 148, actuator grip 158, and pin retainer plates 161, 162 are preferably integrally formed as a single unitary structure from a relatively rigid, lightweight, high-strength material, such as a plastic, which is the same or similar to that used to form the exterior rotation plates 34, 36 and rotation limiting assemblies 92, 93. The rotation lock pins 76 are preferably separate relatively rigid rods formed from a lightweight, high-strength material, such as a metal, e.g. steel or aluminum. The rotation lock pins 76 are sized and configured to be received within the lock notches 132 on the peripheral edge 59 of the interior rotation plate 38. Operation of the rotation locking mechanism is effected by the positioning of the rotation lock pins 76 relative to the lock notches 132. In particular, placement of the rotation lock pins 76 and lock notches 132 in an unlocked position, wherein the rotation lock pins 76 are radially separated from the adjacent lock notches 132, enables an unlocked mode of operation of the rotation locking mechanism. Placement of the rotation lock pins 76 and lock notches 132 in a locked position, wherein the rotation lock pins 76 are fitted within adjacent lock notches 132, enables a locked mode of operation of the rotation locking mechanism.

Method of Operation

Figure 10:
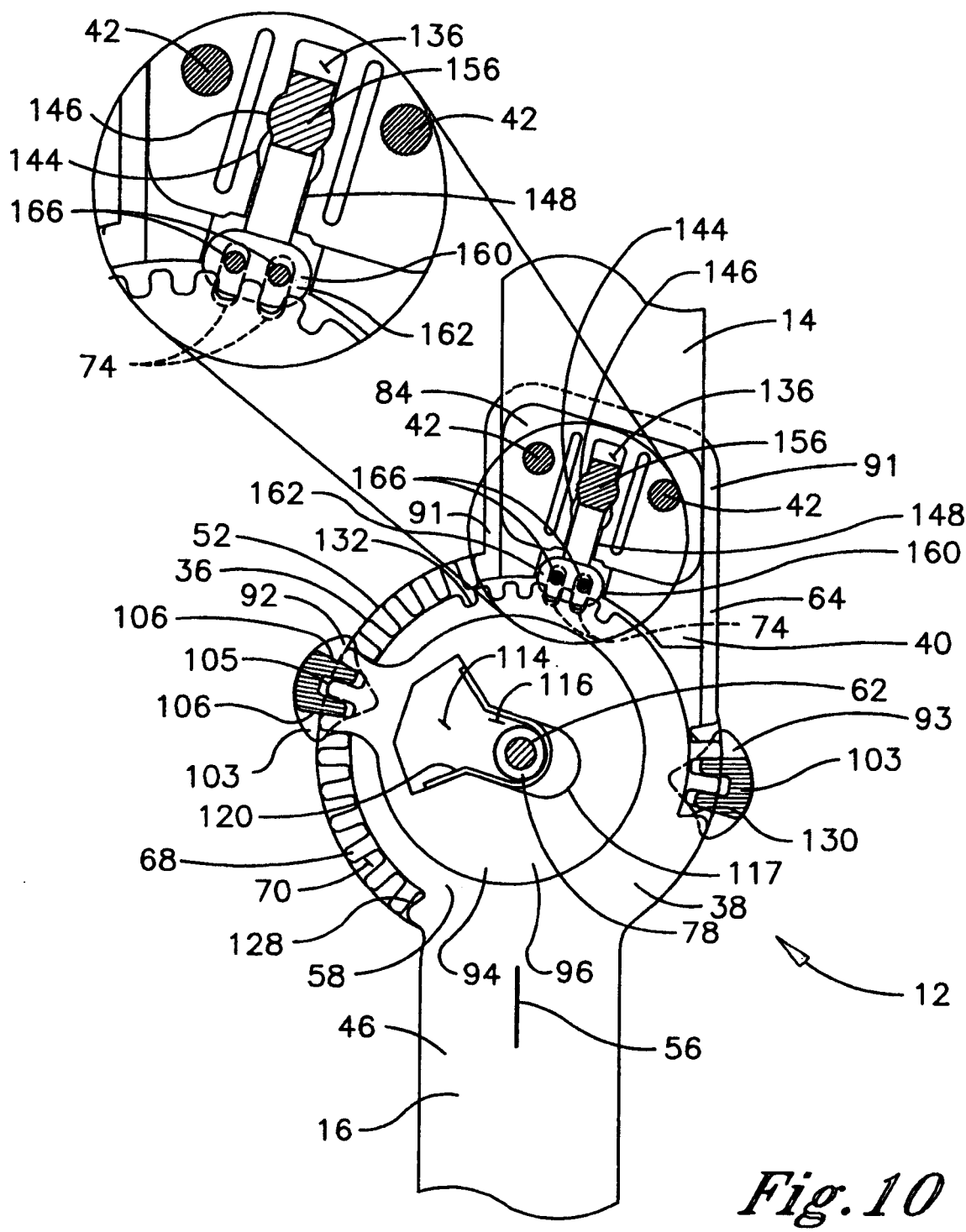
FIG. 10 is a cutaway frontal view of the hinge of FIG. 1, wherein a rotation limiting mechanism of the hinge is in a rotation mode of operation and a rotation locking mechanism of the hinge is in an unlocked mode of operation.

The modes of operation of the above-described hinge 12 and the corresponding positions of the hinge components are described hereafter with reference to the Figures. Referring initially to FIG. 10 in association with FIGS. 1–9, the rotation limiting mechanism of the hinge 12 is shown in the rotation mode of operation and the rotation locking mechanism of the hinge 12 is shown in the unlocked mode of operation. For clarity, the lateral exterior rotation plate 34, actuator grip 158 and lateral pin retainer plate 161 have been removed from the hinge 12 in the view of FIG. 10.

In accordance with the rotation mode of operation, the flexion and extension rotation limiting assemblies 92, 93 are in the fixed position. More particularly, with specific reference to the flexion rotation limiting assembly 92, the rotation mode of operation comprises rotatably positioning the pivot housing 78 of the medial exterior rotation plate 36, which encloses the pivot member 62, within the central channel 116 of the spring cut-out 114 in the rotation limiting assembly plate 94 of the flexion rotation limiting assembly 92 such that the pivot housing 78 is spaced a distance away from the closed end 117.

The rotation mode of operation further comprises fitting a portion of the peripheral edge 52 aligned with a receiving space 70 of the medial exterior rotation plate 36 within the lateral stop slot 104 of the flexion rotation limiting assembly 92, fitting a desired rotation limiting tooth 68 of the medial exterior rotation plate 36 within the lateral tooth slot 105 of the flexion rotation limiting assembly 92, and fitting the lateral engagement faces 106 of the flexion rotation limiting assembly 92 within the receiving spaces 70 of the medial exterior rotation plate 36 adjacent to the rotation limiting tooth 68 in the lateral tooth slot 105. In addition, the lateral head 103 of the flexion rotation limiting assembly 92 is positioned adjacent to the outer face 50 of the medial exterior rotation plate 36. The biasing force of the leaf spring 120 maintains the position of the rotation limiting assembly plate 94 fixed relative to the pivot member 62 and pivot housing 78 preventing inadvertent repositioning of the rotation limiting assembly plate 94 during the rotation mode of operation.

Although not shown in FIG. 10, the rotation mode of operation further comprises fitting a portion of the peripheral edge 52 aligned with the corresponding receiving space 70 of the lateral exterior rotation plate 34 within the medial stop slot 110 of the flexion rotation limiting assembly 92, fitting the corresponding rotation limiting tooth 68 of the lateral exterior rotation plate 34 within the lateral tooth slot 105 of the flexion rotation limiting assembly 92, and fitting the lateral engagement faces 106 of the flexion rotation limiting assembly 92 within the corresponding receiving spaces 70 of the lateral exterior rotation plate 34. In addition, the medial head 112 is positioned adjacent to the outer face 50 of the lateral exterior rotation plate 34. Only the lateral head 103 of the extension rotation limiting assembly 93 is shown in FIG. 10. However, it is understood that the components of the extension rotation limiting assembly 93, which correspond to like components of the flexion rotation limiting assembly 92, are positioned in a substantially similar manner to the above description relating to the flexion rotation limiting assembly 92.

In accordance with the unlocked mode of operation, the lock actuator assembly 88 is in a distal or unlocked position. More particularly, the unlocked mode of operation comprises placing the actuator grip 158 connected to the distal end 152 of the actuator bar 148 at a distal position adjacent to the outer face 50 of the lateral exterior rotation plate 34. Distal positioning of the actuator grip 158 concurrently positions the extended ends 166 of the rotation lock pins 76 mounted within the lock pin retainer 160 at the proximal end 150 of the actuator bar 148 toward the distal end of the lock pin slots 74 in the medial exterior rotation plate 36. Although not shown, it is understood that the extended ends 166 of the rotation lock pins 76 are also positioned toward the distal end of the lock pin slots 74 in the lateral exterior rotation plate 34.

The above-recited distal positions of the actuator grip 158 and rotation lock pins 76 are maintained by tightly fitting the protrusions 156 on the longitudinal sides 154 of the actuator bar 148 near the distal end 152 into the distal indentation 146 along the bordering edges 142 of the lock assembly cut-out 136 in the lock transition plate 84 to inhibit inadvertent slidable displacement of the actuator bar 148 and the associated actuator grip 158 and rotation lock pins 76 during the unlocked mode of operation. The effect of distally positioning the actuator grip 158 and rotation lock pins 76 as recited above is to radially separate the rotation lock pins 76 a sufficient distance from the lock notches 132 in the peripheral edge 59 of the interior rotation plate 38 so that the rotation locking mechanism does not substantially impede the rotation mode of operation of the rotation limiting mechanism, when the rotation locking mechanism is in the unlocked mode of operation. It is further noted that the medial pin retainer plate 162 is medially positioned essentially clear of the peripheral edge 59 of the interior rotation plate 38 and the lateral pin retainer plate 161 (not shown in FIG. 19) is laterally positioned essentially clear of the peripheral edge 59 so that neither pin retainer plate 161, 162 impedes rotation of the hinge 12 at any time during hinge operation.

Figure 11:
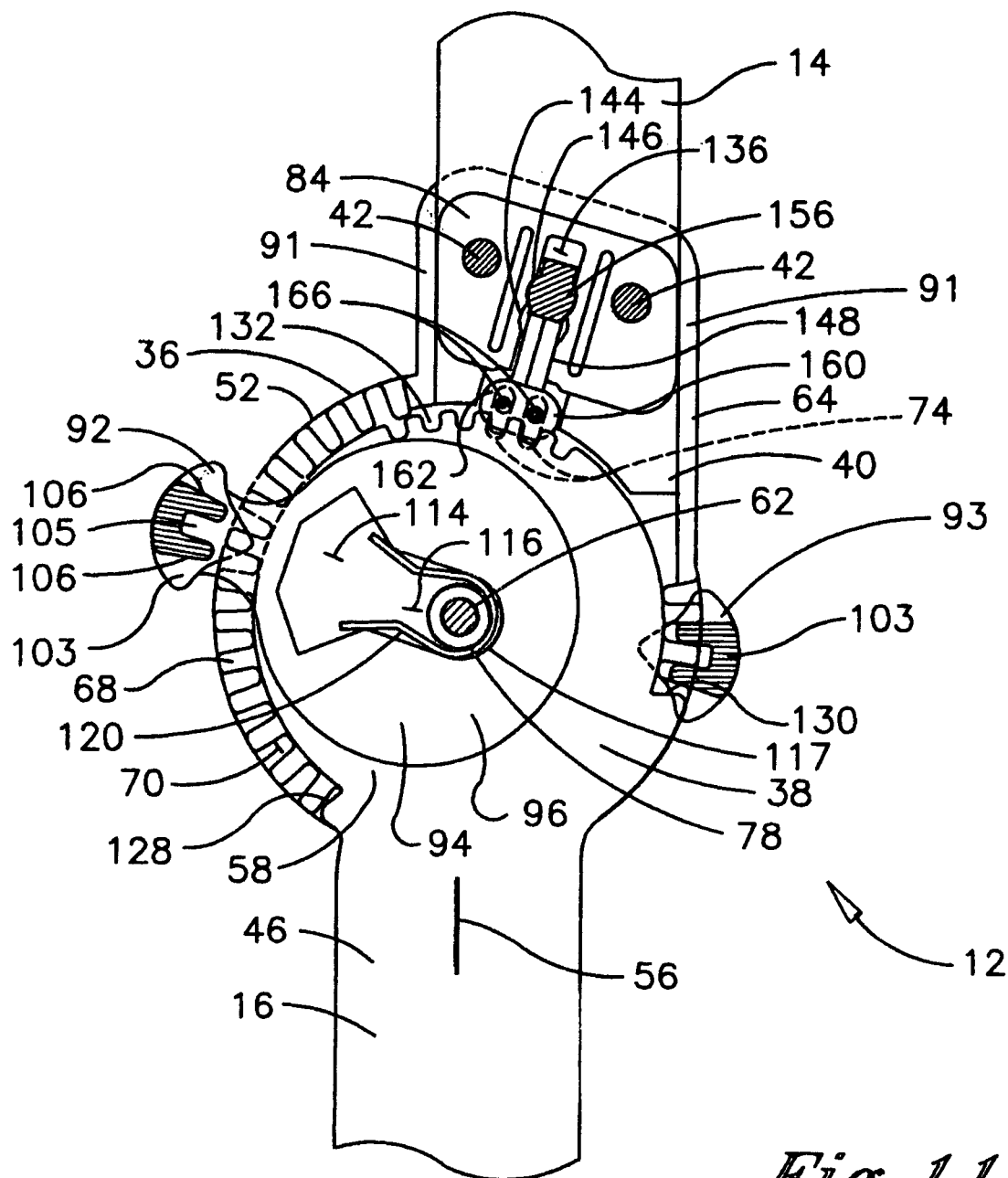
FIG. 11 is a cutaway frontal view of the hinge of FIG. 1, wherein the rotation limiting mechanism is in a rotation limit adjustment mode of operation and the rotation locking mechanism is in the unlocked mode of operation.

Referring to FIG. 11, the rotation limiting mechanism of the hinge 12 is shown in the rotation limit adjustment mode of operation, while the rotation locking mechanism of the hinge 12 is shown in the unlocked mode of operation. In accordance with the present depiction of the rotation limit adjustment mode of operation, the extension rotation limiting assembly 93 remains in the fixed position, while the flexion rotation limiting assembly 92 has been transitioned to the rotation limit adjustment position. However, it is readily apparent to the skilled artisan from the following description that the rotation limit adjustment mode of operation further encompasses transitioning the extension rotation limiting assembly 93 to the rotation limit adjustment position while the flexion rotation limiting assembly 92 remains in the fixed position or transitioning both the flexion and extension rotation limiting assemblies 92, 93 to the rotation limit adjustment position simultaneously. It is also apparent that the rotation locking mechanism of the hinge 12 can alternatively be in the locked mode of operation described hereafter, when the rotation limiting mechanism of the hinge 12 is in the rotation limit adjustment mode of operation.

With specific reference to the flexion rotation limiting assembly 92, the rotation limit adjustment mode of operation comprises displacing the rotation limiting assembly plate 94 of the flexion rotation limiting assembly 92 radially outward by applying a radially outward directed manual force to the medial head 103 to overcome the biasing force of the leaf spring 120. The leaf spring 120 is increasingly tensioned as the closed end 117 of the central channel 116 of the spring cut-out 114 in the rotation limiting assembly plate 94 of the flexion rotation limiting assembly 92 is displaced toward the pivot housing 78 of the medial exterior rotation plate 36. At the same time, the lateral engagement faces 106 are radially withdrawn from the receiving spaces 70 and the corresponding rotation limiting tooth 68 is radially withdrawn from the lateral tooth slot 105. Transitioning the flexion rotation limiting assembly 92 to the rotation limit adjustment position enables rotation of the flexion rotation limiting assembly 92 about the pivot member 62 and pivot housing 78.

Although not shown in FIG. 11, the rotation limit adjustment mode of operation may additionally or alternatively comprise displacing the rotation limiting assembly plate 94 of the flexion rotation limiting assembly 92 radially outward by applying a radially outward directed manual force to the medial head 112 to overcome the biasing force of the leaf spring 120. Increasingly tensioning the leaf spring 120 and displacing the closed end 117 of the central channel 116 toward the pivot housing 78 also simultaneously radially withdraws the medial engagement faces 109 from the corresponding receiving spaces 70 and the corresponding rotation limiting tooth 68 from the medial tooth slot 108.

Figure 12:
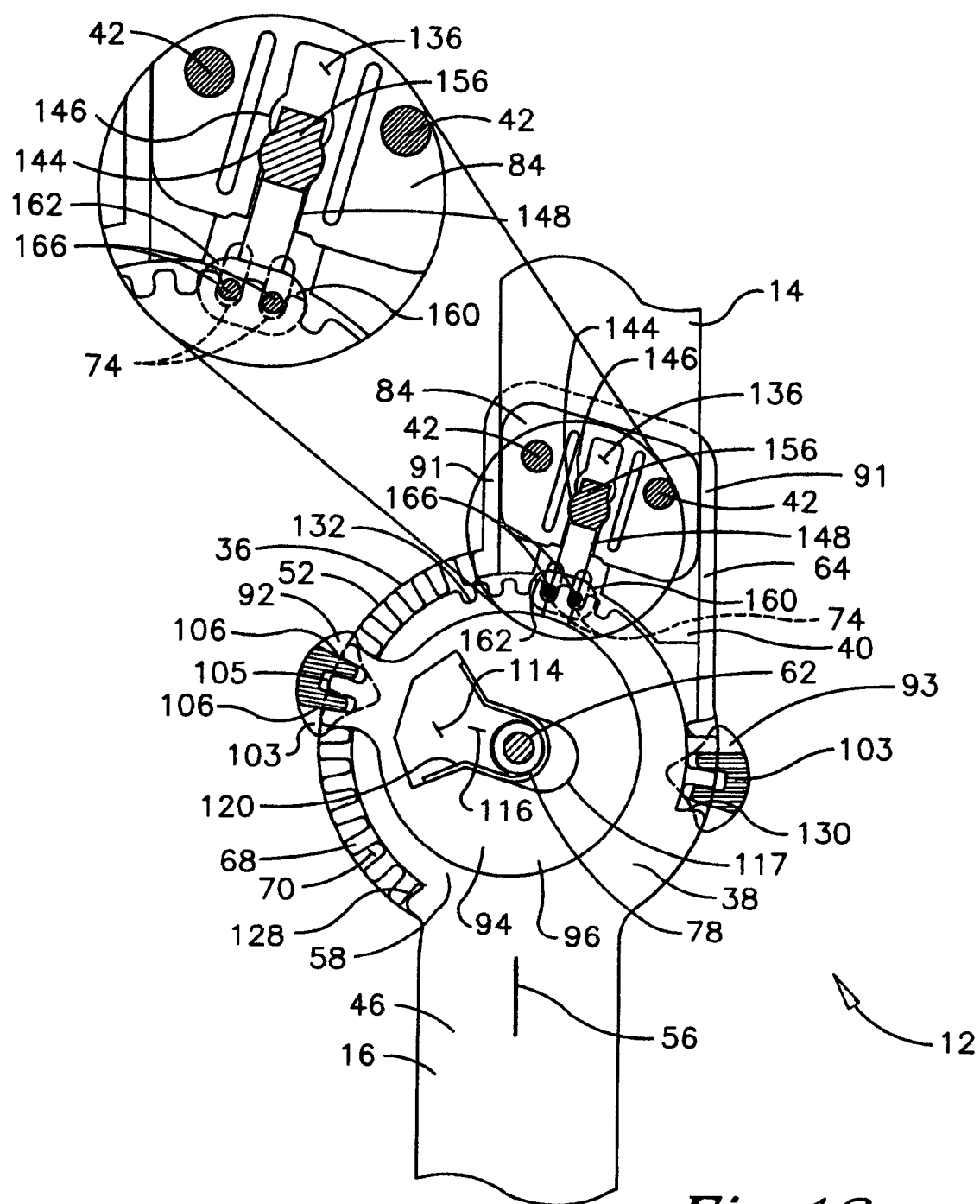
FIG. 12 is a cutaway frontal view of the hinge of FIG. 1, wherein the rotation limiting mechanism is in the rotation mode of operation and the rotation locking mechanism is in a locked mode of operation.

Referring to FIG. 12, the rotation limiting mechanism of the hinge 12 is shown in the rotation mode of operation, while the rotation locking mechanism of the hinge 12 is shown in the locked mode of operation. In accordance with the locked mode of operation, the lock actuator assembly 88 is transitioned from the distal or unlocked position to a proximal or locked position. More particularly, the locked mode of operation comprises manually gripping the actuator grip 158 and slidably displacing the actuator grip 158 in a radially inward direction from the distal position to a proximal position which is likewise adjacent to the outer face 50 of the lateral exterior rotation plate 34. Displacement of the actuator grip 158 is enabled by applying a manual displacement force to the actuator grip 158 which is sufficient to cause the protrusions 156 to press against the bordering edges 142 of the lock assembly cut-out 136 in the lock transition plate 84 and bow the expansion rails 140 outward in cooperation with the expansion slots 138. This provides sufficient clearance for the protrusions 156 to slide out of the distal indentation 146 and travel inwardly through the lock assembly cut-out 136 to the proximal indentation 144.

Displacement of the actuator grip 158 concurrently effects slidable displacement of the extended ends 166 of the rotation lock pins 76 in a radially inward direction toward the proximal end of the lock pin slots 74 in the lateral and medial exterior rotation plates 34, 36. The above-recited proximal positions of the actuator grip 158 and rotation lock pins 76 are maintained by tightly fitting the protrusions 156 on the actuator bar 148 into the proximal indentation 144 to inhibit inadvertent slidable displacement of the actuator bar 148 and the associated actuator grip 158 and rotation lock pins 76 during the locked mode of operation. The effect of proximally positioning the actuator grip 158 and rotation lock pins 76 as recited above is to engage the rotation lock pins 76 within the lock notches 132 in the peripheral edge 59 of the interior rotation plate 38 so that the rotation locking mechanism substantially prevents the rotation mode of operation of the rotation limiting mechanism, when the rotation locking mechanism is in the locked mode of operation.

The rotation locking mechanism enables the practitioner to select a desired locking point for the hinge 12 having a specific degree of rotation from a range of available locking points. The selected locking point is indicated by alignment of the lock reference marker 56 on the proximal end 46 of the lower rotation arm 16 with the selected rotation lock marker 56 on the outer face 50 of the lateral exterior rotation plate 34. An exemplary range of locking points available for selection is between −10° and 30° of extension, wherein the sequential locking points are at graduated intervals of 10°.

The modes of operation of the rotation limiting and locking mechanisms of the hinge 12 are further described hereafter by way of example with reference to FIGS. 13–16. Referring initially to FIG. 13 in association with FIGS. 1–12, the rotation limiting mechanism is in the rotation mode of operation. The lower rotation arm 16 of the brace 10 is rotated about the hinge 12 in a first direction of rotation, which is clockwise as indicated by the arrow 168, until the hinge 12 reaches a preselected first flexion rotation limit where the flexion rotation limiting face 128 on the peripheral edge 59 of the interior rotation plate 38 engages the stop face 107 on the flexion rotation limiting assembly 92. The first flexion rotation limit is preselected in accordance with the rotation limit adjustment mode of operation described above. In the example of FIG. 13, the first flexion rotation limit is 60° as indicated by alignment of the lateral head 103 of the flexion rotation limiting assembly 92 with the 60° flexion rotation limit marker 53 on the outer face 50 of the lateral exterior rotation plate 34. An exemplary range of flexion rotation limits available for selection is between −10° and 120°, wherein the sequential flexion rotation limits are at graduated intervals of 10°.

As noted above, each rotation limiting tooth 68 on the lateral exterior rotation plate 34 is uniquely correlated with a specific flexion or extension rotation limit of the hinge 12 and each flexion rotation limit marker 53 on the lateral exterior rotation plate 34 is aligned with the unique rotation limiting tooth 68 correlated with the flexion rotation limit value displayed by the marker 53. Thus, for example, when the lateral head 103 of the flexion rotation limiting assembly 92 is aligned with the flexion rotation limit marker 53 displaying a flexion rotation limit value of 60°, the rotation limiting tooth 68 correlated with the 60° flexion rotation limit is fitted in the lateral tooth slot 105 of the flexion rotation limiting assembly 92, and the hinge 12 is rotated to 60° flexion, the flexion rotation limiting face 128 on the peripheral edge 59 of the interior rotation plate 38 engages the stop face 107 of the flexion rotation limiting assembly 92.

Referring to FIG. 14, the rotation limiting mechanism remains in the rotation mode of operation. The lower arm 16 of the brace 10 is rotated about the hinge 12 in a second direction of rotation, which is counterclockwise as indicated by the arrow 170, until the hinge 12 reaches a preselected first extension rotation limit where the extension rotation limiting face 130 on the peripheral edge 59 of the interior rotation plate 38 engages the stop face 107 on the extension rotation limiting assembly 93. The first extension rotation limit is likewise preselected in accordance with the rotation limit adjustment mode of operation described above. In the example of FIG. 14, the first extension rotation limit is 10° as indicated by alignment of the lateral head 103 of the extension rotation limiting assembly 93 with the 10° extension rotation limit marker 54 on the outer face 50 of the lateral exterior rotation plate 34. An exemplary range of extension rotation limits available for selection is between −10° and 30°, wherein the sequential extension rotation limits are at graduated intervals of 10°.

As noted above, each rotation limiting tooth 68 on the lateral exterior rotation plate 34 is uniquely correlated with a specific flexion or extension rotation limit of the hinge 12 and each extension rotation limit marker 54 on the lateral exterior rotation plate 34 is aligned with the unique rotation limiting tooth 68 correlated with the extension rotation limit value displayed by the marker 54. Thus, for example, when the lateral head 103 of the extension rotation limiting assembly 93 is aligned with the extension rotation limit marker 54 displaying an extension rotation limit value of 10°, the rotation limiting tooth 68 correlated with the 10° extension rotation limit is fitted in the lateral tooth slot 105 of the extension rotation limiting assembly 93, and the hinge 12 is rotated to 10° extension, the extension rotation limiting face 130 on the peripheral edge 59 of the interior rotation plate 38 engages the stop face 107 of the extension rotation limiting assembly 93.

It is further noted with reference to FIG. 14 that each pair of lock notches 132 on the peripheral edge 59 of the interior rotation plate 38 is uniquely correlated with a specific lock position of the hinge 12. In addition, the position of each rotation lock marker 55 relative to the rotation lock pins 76 is likewise uniquely correlated with a specific lock position of the hinge 12. Thus, for example, when the hinge 12 is rotated to 10° extension, the rotation lock marker 55 displaying a lock position value of 10° extension is aligned with the lock reference marker 56 on the lower rotation arm 16 and the rotation lock pins 76 are aligned with the pair of lock notches 132 correlated with a lock position corresponding to 10° extension. Once this alignment of the rotation lock marker 55, lock reference marker 56, rotation lock pins 76, and pair of lock notches 132 is achieved, the rotation locking mechanism can be transitioned to the locked mode of operation in the manner described above.

It is apparent that the elements of the rotation locking mechanism are structurally distinct from the elements of the rotation limiting mechanism. Thus, none of the structural elements of the rotation locking mechanism are employed in the operation of the rotation limiting mechanism and vice versa. As a result, the lock position of the hinge 12 can be selected independent of the flexion and extension rotation limits of the hinge 12 as long as the selected value of the lock position is less than or equal to the value of the flexion or extension rotation limit. This is an advantageous feature of the present hinge because in most cases the practitioner is able to select the value of the lock position without changing the value of the flexion or extension rotation limit.

Referring to FIG. 15, the rotation limiting mechanism is transitioned to the rotation limit adjustment mode of operation, wherein the preselected first flexion rotation limit of FIG. 13 is adjusted to a second flexion rotation limit in the clockwise direction of the arrow 168 in accordance with the rotation limit adjustment mode of operation described above. In the example of FIG. 15, the second flexion rotation limit is 110° as indicated by alignment of the lateral head 103 of the flexion rotation limiting assembly 92 with the 110° flexion rotation limit marker 53 on the outer face 50 of the lateral exterior rotation plate 34. Adjustment of the extension rotation limit can also be performed in a like manner to the above-described adjustment of the flexion rotation limit, as is readily apparent to the skilled artisan. Upon completion of the rotation limit adjustment mode of operation, operation of the rotation limiting mechanism is resumed in the rotation mode with the hinge 12 having an adjusted flexion and/or extension rotation limit.

Referring to FIG. 16, the rotation limiting mechanism resumes the rotation mode of operation. The lower arm 16 of the brace 10 is rotated about the hinge 12 until the hinge 12 reaches the second flexion rotation limit selected in accordance FIG. 15 where the flexion rotation limiting face 128 on the peripheral edge 59 of the interior rotation plate 38 again engages the stop face 107 on the flexion rotation limiting assembly 92 in substantially the same as described above with reference to FIG. 13.

While the forgoing preferred embodiments of the invention have been described and shown, it is understood that alternatives and modifications, such as those suggested and others, may be made thereto and fall within the scope of the invention. For example, the hinge 12 has been described above as having a pair of rotation lock pins 76 and a pair of rotation limiting assemblies 92, 93. However, a hinge having only a single rotation lock pin and/or a single rotation limiting assembly is alternatively within the purview of the skilled artisan and within the scope of the present invention. The hinge 12 has also been described above as having a pair of external rotation plates 34, 36 and an internal rotation plate 38. However, a hinge having only a single external rotation plate and internal rotation plate is alternatively within the purview of the skilled artisan and within the scope of the present invention. It is likewise readily apparent to the skilled artisan to modify or eliminate elements of the hinge, which are cooperative with the eliminated external rotation plate, rotation limiting assembly and/or rotation lock pin of the alternate embodiments. For example, the flexion and/or extension rotation limiting assemblies 92, 93, rotation lock pins 76, or lock actuator assembly 84 can be modified to accommodate such alternate embodiments.

A hinge having two external rotation plates and a single internal rotation plate, but wherein only one of the external rotation plates includes the rotation limiting teeth 68, receiving spaces 70, and/or lock pin slots 74, is alternatively within the purview of the skilled artisan and within the scope of the present invention. In accordance with these alternate embodiments, one external rotation plate can include the rotation limiting teeth 68, receiving spaces 70, and lock pin slots 74, thereby supporting both the rotation limiting and rotation locking functions of the hinge, while the other external rotation plate is devoid of rotation limiting teeth, receiving spaces, and lock pin slots, thereby supporting neither the rotation limiting function nor the rotation locking function of the hinge. Alternatively, one external rotation plate can include the rotation limiting teeth 68 and receiving spaces 70, but not the lock pin slots 74, thereby only supporting the rotation limiting function of the hinge, while the other external rotation plate includes the lock pin slots 74, but not the rotation limiting teeth 68 and receiving spaces 70, thereby only supporting the rotation locking function of the hinge.

We claim:

1. A hinge for an orthopedic brace comprising:
   a first rotation plate having a first peripheral edge, an inner face and an outer face;
   a second rotation plate having a second peripheral edge;
   a pivotal connector connecting said first and second rotation plates;
   a rotation limiting mechanism including,
      a series of rotation limiting teeth formed in said inner face at said first peripheral edge,
      a rotation limiting face formed in said second peripheral edge, and
      a rotation limiting assembly having an engagement face selectively positionable between two adjacent teeth of said series of said teeth to place said rotation limiting assembly in a fixed position and having a stop face engageable with said rotation limiting face upon rotation of said second rotation plate relative to said first rotation plate in a first rotation direction to substantially limit further rotation of said second rotation plate relative to said first rotation plate in said first rotation direction; and
   a rotation locking mechanism including,
      a series of lock notches formed in said second peripheral edge,
      a lock pin slot formed in said inner face, and
      a rotation lock pin slidably positioned in said lock pin slot and selectively positionable within one of said series of lock notches to substantially lock said first and second rotation plates against rotation of said second rotation plate relative to said first rotation plate in said first rotation direction or in a second rotation direction opposite said first rotation direction.

2. The hinge of claim 1 wherein said rotation limiting mechanism further includes a biasing member biasing said engagement face radially inward from said first peripheral edge.

3. The hinge of claim 1 wherein said rotation locking mechanism further includes a lock actuator assembly engaging said rotation lock pin, wherein said rotation lock pin has a longitudinal axis, said lock actuator assembly maintaining said longitudinal axis of said rotation lock pin substantially perpendicular to said inner face.

4. The hinge of claim 1 wherein said rotation locking mechanism further includes a lock actuator assembly engaging said rotation lock pin, wherein said rotation lock pin has a longitudinal axis and said lock pin slot has a longitudinal axis, said lock actuator assembly maintaining said longitudinal axis of said rotation lock pin substantially perpendicular to said longitudinal axis of said lock pin slot.

5. The hinge of claim 1 wherein said rotation locking mechanism further includes a lock transition plate and a lock actuator assembly engaging said rotation lock pin, wherein said lock transition plate has a lock assembly cut-out and said lock actuator assembly has an actuator bar selectively and slidably positioned in said lock assembly cut-out.

6. The hinge of claim 5 wherein said lock assembly cut-out has a bordering edge with a first depression and a second depression formed therein and said actuator bar has a protrusion configured for close fitting within said first depression and said second depression when said actuator bar is selectively slid within said lock assembly cut-out.

7. The hinge of claim 1 wherein said rotation lock pin is transitionable between a locked position, wherein said rotation lock pin is selectively positioned within said one of said series of lock notches, and an unlocked position, wherein said rotation lock pin is selectively withdrawn from said one of said series of lock notches, without substantially modifying said fixed position of said rotation limiting assembly.

8. A hinge for an orthopedic brace comprising:
   a first rotation plate having a first peripheral edge, an inner face and an outer face;
   a second rotation plate having a second peripheral edge;
   a pivotal connector connecting said first and second rotation plates;
   a rotation limiting mechanism including,
      a rotation limiting face formed in said second peripheral edge, and
      a rotation limiting assembly selectively positionable in a fixed position relative to said first rotation plate and having a stop face engageable with said rotation limiting face upon rotation of said second rotation plate relative to said first rotation plate in a first rotation direction to substantially limit further rotation of said second rotation plate relative to said first rotation plate in said first rotation direction; and
   a rotation locking mechanism including,
      a series of lock notches formed in said second peripheral edge, and
      a rotation lock pin selectively positionable within one of said series of lock notches to substantially lock said first and second rotation plates against rotation of said second rotation plate relative to said first rotation plate in said first rotation direction or in a second rotation direction opposite said first rotation direction.

9. The hinge of claim 8 wherein said rotation limiting mechanism further includes a biasing member biasing said engagement face radially inward from said first peripheral edge.

10. The hinge of claim 8 wherein said rotation locking mechanism further includes a lock actuator assembly engaging said rotation lock pin, wherein said rotation lock pin has a longitudinal axis, said lock actuator assembly maintaining said longitudinal axis of said rotation lock pin substantially perpendicular to said inner face.

11. The hinge of claim 8 wherein said rotation locking mechanism further includes a lock transition plate and a lock actuator assembly engaging said rotation lock pin, wherein said lock transition plate has a lock assembly cut-out and said lock actuator assembly has an actuator bar selectively and slidably positioned in said lock assembly cut-out.

12. The hinge of claim 11 wherein said lock assembly cut-out has a bordering edge with a first depression and a second depression formed therein and said actuator bar has a protrusion configured for close fitting within said first depression and said second depression when said actuator bar is selectively slid within said lock assembly cut-out.

13. The hinge of claim 8 wherein said rotation lock pin is transitionable between a locked position, wherein said rotation lock pin is selectively positioned within said one of said series of lock notches, and an unlocked position, wherein said rotation lock pin is selectively withdrawn from said one of said series of lock notches, without substantially modifying said fixed position of said rotation limiting assembly.

14. A hinge for an orthopedic brace comprising:
   a first rotation arm;
   a second rotation arm;
   a pivotal connector rotatably connecting said first and second rotation arms;
   a first rotation plate fixably connected to said first rotation arm and having a first peripheral edge, an inner face and an outer face;

a second rotation plate rotatably connected to said first rotation plate, said second rotation plate fixably connected to said second rotation arm and having a second peripheral edge; and a rotation locking mechanism comprising,
- a series of lock notches formed in said second peripheral edge;
- a lock pin slot formed in said inner face; and
- a rotation lock pin transitionable between a locked position and an unlocked position, wherein said rotation lock pin is slidably retained in said lock pin slot during both said locked position and said unlocked position and wherein said lock pin is selectively positionable within any one of said series of lock notches when in said locked position to substantially lock said first and second rotation plates against rotation relative to one another in a first rotation direction and in a second rotation direction opposite said first rotation direction and correspondingly to substantially lock said first and second rotation arms against rotation relative to one another in said first and second rotation directions, further wherein said rotation lock pin is selectively withdrawn from said one of said series of lock notches when in said unlocked position.

15. The hinge of claim 14 wherein said rotation locking mechanism further comprises a lock actuator assembly engaging said rotation lock pin, wherein said rotation lock pin has a longitudinal axis, said lock actuator assembly maintaining said longitudinal axis of said rotation lock pin substantially perpendicular to said inner face.

16. The hinge of claim 14 wherein said rotation locking mechanism further includes a lock transition plate and a lock actuator assembly engaging said rotation lock pin, wherein said lock transition plate has a lock assembly cut-out and said lock actuator assembly has an actuator bar selectively and slidably positioned in said lock assembly cut-out.

17. The hinge of claim 16 wherein said lock assembly cut-out has a bordering edge with a first depression and a second depression formed therein and said actuator bar has a protrusion configured for close fitting within said first depression and said second depression when said actuator bar is selectively slid within said lock assembly cut-out.

18. A hinge for an orthopedic brace comprising:
a first external rotation plate having a first external peripheral edge, a first external inner face and a first external outer face;

an internal rotation plate having an internal peripheral edge;

a second external rotation plate having a second external peripheral edge, a second external inner face and a second external outer face;

a pivotal connector connecting said first and second external rotation plates and said internal rotation plate;

a rotation limiting mechanism including,
- a series of rotation limiting teeth formed in said first external inner face at said first external peripheral edge,
- a rotation limiting face formed in said internal peripheral edge, and
- a rotation limiting assembly having an engagement face selectively positionable between two adjacent teeth of said series of said teeth to place said rotation limiting assembly in a fixed position and having a stop face engageable with said rotation limiting face upon rotation of said internal rotation plate relative to said first external rotation plate in a first rotation direction to substantially limit further rotation of said internal rotation plate relative to said first external rotation plate in said first rotation direction; and a rotation locking mechanism including,
- a series of lock notches formed in said internal peripheral edge,
- a lock pin slot formed in said first and/or second external inner face, and
- a rotation lock pin slidably positioned in said lock pin slot and selectively positionable within one of said series of lock notches to substantially lock said first external rotation plate and said internal rotation plate against rotation of said internal rotation plate relative to said first external rotation plate in said first rotation direction or in a second rotation direction opposite said first rotation direction.

19. The hinge of claim 18 wherein said engagement face is a first engagement face, said rotation limiting mechanism further including a series of rotation limiting teeth formed in said second external inner face at said second external peripheral edge, a second engagement face of said rotation limiting assembly selectively positionable between two adjacent teeth of said series of said teeth in said second external inner face.

* * * * *

UNITED STATES PATENT AND TRADEMARK OFFICE
CERTIFICATE OF CORRECTION

PATENT NO. : 7,235,059 B2  
APPLICATION NO. : 11/039448  
DATED : June 26, 2007  
INVENTOR(S) : Jeffrey T. Mason et al.

Page 1 of 1

It is certified that error appears in the above-identified patent and that said Letters Patent is hereby corrected as shown below:

Column 14, line 64: delete "of the"  
Column 16, line 54: delete "FIG. 19" and insert --FIG. 10--  
Column 17, line 17: delete "medial" and insert --lateral--

Signed and Sealed this

Sixth Day of July, 2010

David J. Kappos  
*Director of the United States Patent and Trademark Office*

(12) EX PARTE REEXAMINATION CERTIFICATE (6995th)
United States Patent
Mason et al.

(10) Number: US 7,235,059 C1
(45) Certificate Issued: Aug. 11, 2009

(54) RELEASABLY LOCKING HINGE FOR AN ORTHOPEDIC BRACE HAVING ADJUSTABLE ROTATION LIMITS

(75) Inventors: Jeffrey T. Mason, Escondido, CA (US); Paul Oddou, Oceanside, CA (US)

(73) Assignee: Wachovia Bank, National Association, as Administrative Agent, Charlotte, NC (US)

Reexamination Request:
No. 90/008,730, Jun. 26, 2007

Reexamination Certificate for:
| Patent No.: | 7,235,059 |
| Issued: | Jun. 26, 2007 |
| Appl. No.: | 11/039,448 |
| Filed: | Jan. 12, 2005 |

(51) Int. Cl.
*A61F 5/00* (2006.01)

(52) U.S. Cl. .......................... 602/26; 602/23; 602/5; 602/16; 128/882

(58) Field of Classification Search .................. None
See application file for complete search history.

(56) References Cited

U.S. PATENT DOCUMENTS

| 2,812,961 A | 11/1957 | Brown et al. |
| 5,672,152 A | 9/1997 | Mason et al. |
| 5,827,208 A | 10/1998 | Mason et al. |
| 5,938,629 A | 8/1999 | Bloedau |

FOREIGN PATENT DOCUMENTS

| WO | WO 02/02035 | 1/2002 |

*Primary Examiner*—Jeffrey R Jastrzab

(57) ABSTRACT

A hinge for an orthopedic brace has two rotation plates, a pivotal connector connecting the rotation plates, a rotation limiting mechanism, and a rotation locking mechanism. The rotation limiting mechanism includes a rotation limiting face formed in one of the rotation plates and a rotation limiting assembly which has a stop face engageable with the rotation limiting face upon rotation of the rotation plates in a given direction to limit further rotation in that direction. The rotation locking mechanism includes a series of lock notches formed in one of the rotation plates and a rotation lock pin positionable within one of the lock notches to lock the rotation plates in a fixed position.

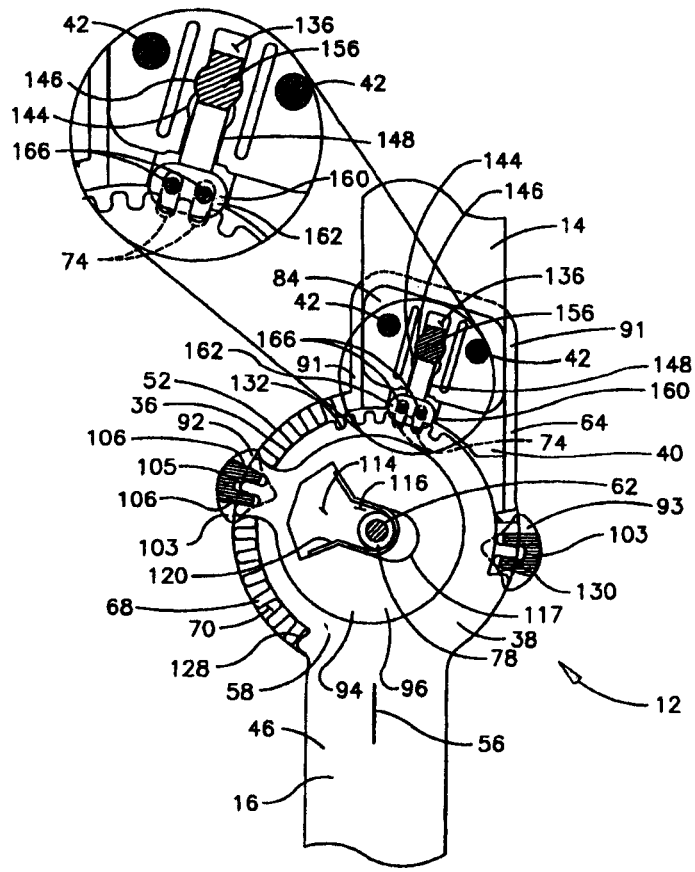

US 7,235,059 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 3, 4, 11–13, 16 and 17 are now disclaimed.

Claims 1, 5, 7, 8, 10, 14, 15 and 18 are determined to be patentable as amended.

New claim 20 is added and determined to patentable.

Claims 2, 6, 9 and 19 were not reexamined.

1. A hinge for an orthopedic brace comprising:
a first rotation plate having a first peripheral edge, an inner face and an outer face;
a second rotation plate having a second peripheral edge;
a pivotal connector connecting said first and second rotation plates;
a rotation limiting mechanism including,
a series of rotation limiting teeth formed in said inner face at said first peripheral edge,
a rotation limiting face formed in said second peripheral edge, and
a rotation limiting assembly having an engagement face selectively positionable between two adjacent teeth of said series of said teeth to place said rotation limiting assembly in a fixed position and having a stop face engageable with said rotation limiting face upon rotation of said second rotation plate relative to said first rotation plate in a first rotation direction *opposite a second rotation direction* to substantially limit further rotation of said second rotation plate relative to said first rotation plate in said first rotation direction; and
a rotation locking mechanism including,
a series of lock notches formed in said second peripheral edge,
a lock pin slot formed in said inner face, [and]
a rotation lock pin [slidably positioned in said lock pin slot and selectively positionable within one of said series of lock notches to substantially lock said first and second rotation plates against rotation of said second rotation plate relative to said first rotation plate in said first rotation direction or in a second rotation direction opposite said first rotation direction] *transitionable between a locked position and an unlocked position, wherein said rotation lock pin is slidably retained in said lock pin slot during both said locked position and said unlocked position and wherein said rotation lock pin is selectively positionable within any one of said series of lock notches when in said locked position to substantially lock said first and second rotation plates against rotation relative to one another in said first and second rotation directions and correspondingly to substantially lock said first and second rotation arms against rotation relative to one another in said first and second rotation directions, further wherein said rotation lock pin is selectively withdrawn from said one of said series of lock notches when in said unlocked position, and*
*a lock actuator assembly having an actuator bar with said rotation lock pin fixably mounted on an end thereof and said actuator bar and said rotation lock pin being selectively and radially slidably displaceable relative to said pivotal connector to transition said rotation lock pin between said locked position and said unlocked position, said rotation lock pin and said actuator bar each have a longitudinal axis aligned essentially perpendicular to one another with said rotation lock pin having an extended end extending perpendicularly away from said actuator bar to be slidably received in said lock pin slot while said actuator bar is maintained external to said lock pin slot, said extended end of said rotation lock pin being slidably displaced within said lock pin slot when transitioning said rotation lock pin between said locked and unlocked positions.*

5. The hinge of claim 1 wherein said rotation locking mechanism further includes a lock transition plate [and a lock actuator assembly engaging said rotation lock pin, wherein said lock transition plate has] *having* a lock assembly cut-out and said [lock actuator assembly has an] actuator bar selectively and slidably positioned in said lock assembly cut-out.

7. The hinge of claim 1 wherein said rotation lock pin is transitionable between [a] *said* locked position[, wherein said rotation lock pin is selectively positioned within said one of said series of lock notches, and an] *and said* unlocked position[, wherein said rotation lock pin is selectively withdrawn from said one of said series of lock notches,] without substantially modifying said fixed position of said rotation limiting assembly.

8. A hinge for an orthopedic brace comprising:
a first rotation plate having a first peripheral edge, an inner face and an outer face;
a second rotation plate having a second peripheral edge;
a pivotal connector connecting said first and second rotation plates;
a rotation limiting mechanism including,
a rotation limiting face formed in said second peripheral edge, and
a rotation limiting assembly selectively positionable in a fixed position relative to said first rotation plate and having a stop face engageable with said rotation limiting face upon rotation of said second rotation plate relative to said first rotation plate in a first rotation direction *opposite a second rotation direction* to substantially limit further rotation of said second rotation plate relative to said first rotation plate in said first rotation direction; and
a rotation locking mechanism including,
a series of lock notches formed in said second peripheral edge, [and]
a rotation lock pin [selectively positionable within one of said series of lock notches to substantially lock said first and second rotation plates against rotation of said second rotation plate relative to said first rotation plate in said first rotation direction or in a second rotation direction opposite said first rotation direction] *transitionable between a locked position and an unlocked position wherein said rotation lock pin is* selectively positionable within any one of said series of lock notches when in said locked position to substantially lock said first and second rotation plates against rotation relative to one another in said and second first rotation directions and correspondingly to substantially lock said first and second rotation arms against rotation relative to one another in said first and second rotation directions, further wherein said rotation lock pin is selectively withdrawn from said one of said series of lock notches when in said unlocked position, a lock transition plate fixably positioned relative to said pivotal connector and having a lock assembly cut-out positioned more radially distant from said pivotal connector than said second peripheral edge and free from engagement with said pivotal connector; and a lock actuator assembly having an actuator bar selectively and slidably positioned in said lock assembly cut-out with said rotation lock pin mounted on an end of said actuator bar, said lock assembly cut-out having an elastically laterally expandable bordering edge with a first depression and a second depression formed therein, said first depression associated with said locked position and said second depression associated with said unlocked position of said rotation lock pin and said actuator bar having a protrusion configured for close fitting within said first depression when said rotation lock pin is in said locked position or close fitting within said second depression when said rotation lock pin is in said unlocked position, said rotation lock pin being transitionable between said locked and unlocked positions by manually sliding said actuator bar within said lock assembly cut-out to displace said protrusion between said first and second depressions.

10. The hinge of claim 8 wherein [said rotation locking mechanism further includes a lock actuator assembly engaging said rotation lock pin, wherein] said rotation lock pin and said actuator bar each have a longitudinal axis *aligned essentially perpendicular to one another with said rotation lock pin having an extended end extending perpendicularly away from said actuator bar to be slidably received in said lock pin slot while said actuator bar is maintained external to said lock pin slot*, said lock actuator assembly maintaining said longitudinal axis of said rotation lock pin substantially perpendicular to said inner face *of said first rotation face while said extended end of said rotation lock pin is slidably displaced within said lock pin slot to transition said rotation lock pin between said locked and unlocked positions.*

14. A hinge for an orthopedic brace comprising:

a first rotation arm;

a second rotation arm;

a pivotal connector rotatably connecting said first and second rotation arms;

a first rotation plate fixably connected to said first rotation arm and having a first peripheral edge, an inner face and an outer face;

a second rotation plate rotatably connected to said first rotation plate, said second rotation plate fixably connected to said second rotation arm and having a second peripheral edge; and a rotation locking mechanism comprising, a series of lock notches formed in said second peripheral edge;

a lock pin slot formed in said inner face; [and]

a rotation lock pin transitionable between a locked position and an unlocked position, wherein said rotation lock pin is slidably retained in said lock pin slot during both said locked position and said unlocked position and wherein said *rotation* lock pin is selectively positionable within any one of said series of lock notches when in said locked position to substantially lock said first and second rotation plates against rotation relative to one another in a first rotation direction and in a second rotation direction opposite said first rotation direction and correspondingly to substantially lock said first and second rotation arms against rotation relative to one another in said first and second rotation directions, further wherein said rotation lock pin is selectively withdrawn from said one of said series of lock notches when in said unlocked position;

a lock transition plate fixably positioned relative to said pivotal connector and having a lock assembly cut-out positioned more radially distant from said pivotal connector than said second peripheral edge and free from engagement with said pivotal connector; and a lock actuator assembly having an actuator bar selectively and slidably positioned in said lock assembly cut-out with said rotation lock pin mounted on an end of said actuator bar, said lock assembly cut-out having an elastically laterally expandable bordering edge with a first depression and a second depression formed therein, said first depression associated with said locked position and said second depression associated with said unlocked position of said rotation lock pin and said actuator bar having a protrusion configured for close fitting within said first depression when said rotation lock pin is in said locked position or close fitting within said second depression when said rotation lock pin is in said unlocked position, said rotation lock pin being transitionable between said locked and unlocked positions by manually sliding said actuator bar within said lock assembly cut-out to displace said protrusion between said first and second depressions.

15. The hinge of claim 14 wherein [said rotation locking mechanism further comprises a lock actuator assembly engaging said rotation lock pin, wherein] said rotation lock pin *and said actuator bar each have* a longitudinal axis *aligned essentially perpendicular to one another with said rotation lock pin having an extended end extending perpendicularly away from said actuator bar to be slidably received in said lock pin slot while said actuator bar is maintained external to said lock pin slot*, said lock actuator assembly maintaining said longitudinal axis of said rotation lock pin substantially perpendicular to said inner face *of said first rotation face while said extended end of said rotation lock pin is slidably displaced within said lock pin slot to transition said rotation lock pin between said locked and unlocked positions.*

18. A hinge for an orthopedic brace comprising:

a first external rotation plate having a first external peripheral edge, a first external inner face and a first external outer face;

an internal rotation plate having an internal peripheral edge;

a second external rotation plate having a second external peripheral edge, a second external inner face and a second external outer face;

a pivotal connector connecting said first and second external rotation plates and said internal rotation plate;

a rotation limiting mechanism including,

> a series of rotation limiting teeth formed in said first external inner face at said first external peripheral edge,
>
> a rotation limiting face formed in said internal peripheral edge, and
>
> a rotation limiting assembly having an engagement face selectively positionable between two adjacent teeth of said series of said teeth to place said rotation limiting assembly in a fixed position and having a stop face engageable with said rotation limiting face upon rotation of said internal rotation plate relative to said first external rotation plate in a first rotation direction opposite a second rotation direction to substantially limit further rotation of said internal rotation plate relative to said first external rotation plate in said first rotation direction; and a rotation locking mechanism including, a series of lock notches formed in said internal peripheral edge, a lock pin slot formed in said first and/or second external inner face, and a rotation lock pin [slidably positioned in said lock pin slot and selectively positionable within one of said series of lock notches to substantially lock said first external rotation plate and said internal rotation plate against rotation of said internal rotation plate relative to said first external rotation plate in said first rotation direction or in a second rotation direction opposite said first rotation direction] *transitionable between a locked position and an unlocked position, wherein said rotation lock pin is slidably retained in said lock pin slot during both said locked position and said unlocked position and wherein said rotation lock pin is selectively positionable within any one of said series of lock notches when in said locked position to substantially lock said first external rotation plate and said internal rotation plate against rotation of said internal rotation plate relative to said first external rotation plate in said first and second rotation directions, further wherein said rotation lock pin is selectively withdrawn from said one of said series of lock notches when in said unlocked position;*

*a lock transition plate fixably positioned relative to said pivotal connector and having a lock assembly cut-out positioned more radially distant from said pivotal connector than said second peripheral edge and free from engagement with said pivotal connector; and*

*a lock actuator assembly having an actuator bar selectively and slidably positioned in said lock assembly cut-out with said rotation lock pin mounted on an end of said actuator bar, said lock assembly cut-out having an elastically laterally expandable bordering edge with a first depression and a second depression formed therein, said first depression associated with said locked position and said second depression associated with said unlocked position of said rotation lock pin and said actuator bar having a protrusion configured for close fitting within said first depression when said rotation lock pin is in said locked position or close fitting within said second depression when said rotation lock pin is in said unlocked position, said rotation lock pin being transitionable between said locked and unlocked positions by manually sliding said actuator bar within said lock assembly cut-out to displace said protrusion between said first and second depressions.*

20. *A hinge for an orthopedic brace comprising:*

*a first rotation arm;*

*a second rotation arm;*

*a pivotal connector rotatably connecting said first and second rotation arms;*

*a first rotation plate fixably connected to said first rotation arm and having a first peripheral edge, an inner face and an outer face;*

*a second rotation plate rotatably connected to said first rotation plate, said second rotation plate fixably connected to said second rotation arm and having a second peripheral edge; and*

*a rotation locking mechanism comprising,*

> *a series of lock notches formed in said second peripheral edge;*
>
> *a lock pin slot formed in said inner face;*
>
> *a rotational lock pin transitionable between a locked position and an unlocked position, wherein said rotation lock pin is slidably retained in said lock pin slot during both said locked position and said unlocked position and wherein said rotation lock pin is selectively positionable within any one of said series of lock notches when in said locked position to substantially lock said first and second rotation plates against rotation relative to one another in a first rotation direction and in a second rotation direction opposite said first rotation direction and correspondingly to substantially lock said first and second rotation arms against rotation relative to one another in said first and second rotation directions, further wherein said rotation lock pin is selectively withdrawn from said one of said series of lock notches when in said unlocked position; and*
>
> *a lock actuator assembly having an actuator bar with said rotation lock pin fixably mounted on an end thereof and said actuator bar and said rotation lock pin being selectively and radially slidably displaceable relative to said pivotal connector to transition said rotation lock pin between said locked position and said unlocked position, said rotation lock pin and said actuator bar each have a longitudinal axis aligned essentially perpendicular to one another with said rotation lock pin having an extended end extending perpendicularly away from said actuator bar to be slidably received in said lock pin slot while said actuator bar is maintained external to said lock pin slot, said extended end of said rotation lock pin being slidably displaced within said lock pin slot when transitioning said rotation lock pin between said locked and unlocked positions.*

\* \* \* \* \*